(12) United States Patent
Palerm et al.

(10) Patent No.: US 9,849,240 B2
(45) Date of Patent: Dec. 26, 2017

(54) DATA MODIFICATION FOR PREDICTIVE OPERATIONS AND DEVICES INCORPORATING SAME

(71) Applicant: MEDTRONIC MINIMED, INC., Northridge, CA (US)

(72) Inventors: Cesar C. Palerm, Pasadena, CA (US); Louis J. Lintereur, Stevenson Ranch, CA (US); Salman Monirabbasi, Playa Vista, CA (US); Kris R. Holtzclaw, Santa Clarita, CA (US); Lane Desborough, Thousand Oaks, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 706 days.

(21) Appl. No.: 14/104,960

(22) Filed: Dec. 12, 2013

(65) Prior Publication Data

US 2015/0165119 A1 Jun. 18, 2015

(51) Int. Cl.
*A61M 5/172* (2006.01)
*A61M 5/142* (2006.01)
*G06F 19/00* (2011.01)

(52) U.S. Cl.
CPC ...... *A61M 5/1723* (2013.01); *A61M 5/14244* (2013.01); *G06F 19/345* (2013.01);
(Continued)

(58) Field of Classification Search
CPC ............ A61M 5/1723; A61M 5/14244; A61M 2005/1726; A61M 2230/201; A61M 5/142; G06F 19/3468
See application file for complete search history.

(56) References Cited

U.S. PATENT DOCUMENTS 3,631,847 A 1/1972 Hobbs, II
4,212,738 A 7/1980 Henne
(Continued)

FOREIGN PATENT DOCUMENTS

DE 4329229 3/1995
EP 0319268 11/1988
(Continued)

OTHER PUBLICATIONS

Kantz, H., et al, (2004). Nonlinear Time Series Analysis. Cambridge. Cambridge University Press. pp. 58-59.*
(Continued)

*Primary Examiner* — Nathan R Price
*Assistant Examiner* — Melissa A Snyder
(74) *Attorney, Agent, or Firm* — Lorenz & Kopf, LLC

(57) ABSTRACT

Infusion systems, infusion devices, and related operating methods are provided. An exemplary method of operating an infusion device capable of delivering fluid to a user involves obtaining a sequence of measurements indicative of a condition of the user that is influenced by the fluid and modifying one or more unusable measurements in the sequence using one or more other usable measurements in the sequence to obtain a modified sequence of measurements. The method continues by determining a predicted value for the condition of the user at a time in the future based at least in part on the modified sequence of measurements and operating the infusion device in a manner that is influenced by the predicted value.

20 Claims, 10 Drawing Sheets

(52) U.S. Cl.
CPC .............. *G06F 19/3468* (2013.01); *A61M 2005/14208* (2013.01); *A61M 2005/1726* (2013.01); *A61M 2205/3303* (2013.01); *A61M 2205/50* (2013.01); *A61M 2230/06* (2013.01); *A61M 2230/201* (2013.01); *A61M 2230/63* (2013.01)

(56) References Cited

U.S. PATENT DOCUMENTS

| | | |
|---|---|---|
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | Decant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,505,709 A | 4/1996 | Funderburk et al. |
| 5,497,772 A | 5/1996 | Schulman et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,248,093 B1 | 6/2001 | Moberg |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |

(56) References Cited

U.S. PATENT DOCUMENTS

| | | | |
|---|---|---|---|
| 6,503,381 B1 | 1/2003 | Gotoh et al. | |
| 6,514,718 B2 | 2/2003 | Heller et al. | |
| 6,544,173 B2 | 4/2003 | West et al. | |
| 6,553,263 B1 | 4/2003 | Meadows et al. | |
| 6,554,798 B1 | 4/2003 | Mann et al. | |
| 6,558,320 B1 | 5/2003 | Causey, III et al. | |
| 6,558,351 B1* | 5/2003 | Steil | A61B 5/14532 604/131 |
| 6,560,741 B1 | 5/2003 | Gerety et al. | |
| 6,565,509 B1 | 5/2003 | Say et al. | |
| 6,579,690 B1 | 6/2003 | Bonnecaze et al. | |
| 6,589,229 B1 | 7/2003 | Connelly et al. | |
| 6,591,125 B1 | 7/2003 | Buse et al. | |
| 6,592,745 B1 | 7/2003 | Feldman et al. | |
| 6,605,200 B1 | 8/2003 | Mao et al. | |
| 6,605,201 B1 | 8/2003 | Mao et al. | |
| 6,607,658 B1 | 8/2003 | Heller et al. | |
| 6,616,819 B1 | 9/2003 | Liamos et al. | |
| 6,618,934 B1 | 9/2003 | Feldman et al. | |
| 6,623,501 B2 | 9/2003 | Heller et al. | |
| 6,641,533 B2 | 11/2003 | Causey, III et al. | |
| 6,654,625 B1 | 11/2003 | Say et al. | |
| 6,659,980 B2 | 12/2003 | Moberg et al. | |
| 6,671,554 B2 | 12/2003 | Gibson et al. | |
| 6,676,816 B2 | 1/2004 | Mao et al. | |
| 6,689,265 B2 | 2/2004 | Heller et al. | |
| 6,728,576 B2 | 4/2004 | Thompson et al. | |
| 6,733,471 B1 | 5/2004 | Ericson et al. | |
| 6,740,072 B2 | 5/2004 | Starkweather et al. | |
| 6,746,582 B2 | 6/2004 | Heller et al. | |
| 6,747,556 B2 | 6/2004 | Medema et al. | |
| 6,749,740 B2 | 6/2004 | Liamos et al. | |
| 6,752,787 B1 | 6/2004 | Causey, III et al. | |
| 6,809,653 B1 | 10/2004 | Mann et al. | |
| 6,817,990 B2 | 11/2004 | Yap et al. | |
| 6,827,702 B2 | 12/2004 | Lebel et al. | |
| 6,881,551 B2 | 4/2005 | Heller et al. | |
| 6,892,085 B2 | 5/2005 | McIvor et al. | |
| 6,893,545 B2 | 5/2005 | Gotoh et al. | |
| 6,895,263 B2 | 5/2005 | Shin et al. | |
| 6,916,159 B2 | 7/2005 | Rush et al. | |
| 6,932,584 B2 | 8/2005 | Gray et al. | |
| 6,932,894 B2 | 8/2005 | Mao et al. | |
| 6,942,518 B2 | 9/2005 | Liamos et al. | |
| 7,052,472 B1* | 5/2006 | Miller | A61B 5/01 600/549 |
| 7,153,263 B2 | 12/2006 | Carter et al. | |
| 7,153,289 B2 | 12/2006 | Vasko | |
| 7,323,142 B2 | 1/2008 | Pendo et al. | |
| 7,396,330 B2 | 7/2008 | Banet et al. | |
| 7,402,153 B2 | 7/2008 | Steil et al. | |
| 7,621,893 B2 | 11/2009 | Moberg et al. | |
| 8,474,332 B2 | 7/2013 | Bente, IV | |
| 8,560,082 B2* | 10/2013 | Wei | A61M 5/142 607/67 |
| 2001/0044731 A1 | 11/2001 | Coffman et al. | |
| 2002/0013518 A1 | 1/2002 | West et al. | |
| 2002/0055857 A1 | 5/2002 | Mault et al. | |
| 2002/0082665 A1 | 6/2002 | Haller et al. | |
| 2002/0137997 A1 | 9/2002 | Mastrototaro et al. | |
| 2002/0161288 A1 | 10/2002 | Shin et al. | |
| 2003/0060765 A1 | 3/2003 | Campbell et al. | |
| 2003/0078560 A1 | 4/2003 | Miller et al. | |
| 2003/0088166 A1 | 5/2003 | Say et al. | |
| 2003/0144581 A1 | 7/2003 | Conn et al. | |
| 2003/0152823 A1 | 8/2003 | Heller | |
| 2003/0176183 A1 | 9/2003 | Drucker et al. | |
| 2003/0188427 A1 | 10/2003 | Say et al. | |
| 2003/0199744 A1 | 10/2003 | Buse et al. | |
| 2003/0208113 A1 | 11/2003 | Mault et al. | |
| 2003/0220552 A1 | 11/2003 | Reghabi et al. | |
| 2004/0061232 A1 | 4/2004 | Shah et al. | |
| 2004/0061234 A1 | 4/2004 | Shah et al. | |
| 2004/0064133 A1 | 4/2004 | Miller et al. | |
| 2004/0064156 A1 | 4/2004 | Shah et al. | |
| 2004/0073095 A1 | 4/2004 | Causey, III et al. | |
| 2004/0074785 A1 | 4/2004 | Holker et al. | |
| 2004/0093167 A1 | 5/2004 | Braig et al. | |
| 2004/0097796 A1 | 5/2004 | Berman et al. | |
| 2004/0102683 A1 | 5/2004 | Khanuja et al. | |
| 2004/0111017 A1 | 6/2004 | Say et al. | |
| 2004/0122353 A1 | 6/2004 | Shahmirian et al. | |
| 2004/0167465 A1 | 8/2004 | Mihai et al. | |
| 2004/0263354 A1 | 12/2004 | Mann et al. | |
| 2005/0038331 A1 | 2/2005 | Silaski et al. | |
| 2005/0038680 A1 | 2/2005 | McMahon et al. | |
| 2005/0043598 A1* | 2/2005 | Goode, Jr. | A61B 5/0031 600/316 |
| 2005/0154271 A1 | 7/2005 | Rasdal et al. | |
| 2005/0192557 A1 | 9/2005 | Brauker et al. | |
| 2005/0203360 A1* | 9/2005 | Brauker | A61B 5/1468 600/345 |
| 2006/0229694 A1 | 10/2006 | Schulman et al. | |
| 2006/0238333 A1 | 10/2006 | Welch et al. | |
| 2006/0293571 A1 | 12/2006 | Bao et al. | |
| 2007/0088521 A1 | 4/2007 | Shmueli et al. | |
| 2007/0135866 A1 | 6/2007 | Baker et al. | |
| 2008/0154503 A1 | 6/2008 | Wittenber et al. | |
| 2009/0081951 A1 | 3/2009 | Erdmann et al. | |
| 2009/0082635 A1 | 3/2009 | Baldus et al. | |
| 2011/0233393 A1 | 9/2011 | Hanson et al. | |
| 2014/0107607 A1 | 4/2014 | Estes | |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |

OTHER PUBLICATIONS

PCT Search Report (PCT/US02/03299), dated Oct. 31, 2002, Medtronic Minimed, Inc.
(Animas Corporation, 1999). Animas . . . bringing new life to insulin therapy.
Bode B W, et al. (1996). Reduction in Severe Hypoglycemia with Long-Term Continuous Subcutaneous Insulin Infusion in Type I Diabetes. Diabetes Care, vol. 19, No. 4, 324-327.
Boland E (1998). Teens Pumping it Up! Insulin Pump Therapy Guide for Adolescents. 2nd Edition.
Brackenridge B P (1992). Carbohydrate Gram Counting a Key to Accurate Mealtime Boluses in Intensive Diabetes Therapy. Practical Diabetology, vol. 11, No. 2, pp. 22-28.
Brackenridge, B P et al. (1995). Counting Carbohydrates How to Zero in on Good Control. MiniMed Technologies Inc.
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.

(56) References Cited

OTHER PUBLICATIONS

Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting a Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed•Technologies.
(Intensive Diabetes Management, 1995). Insulin Infusion Pump Therapy. pp. 66-78.
Disetronic My Choice™ D-TRON™ Insulin Pump Reference Manual. (no date).
Disetronic H-Tron® plus Quick Start Manual. (no date).
Disetronic My Choice H-TRONplus Insulin Pump Reference Manual. (no date).
Disetronic H-TRON® plus Reference Manual. (no date).
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page, Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMer™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump a Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.

Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.

(56) References Cited

OTHER PUBLICATIONS

Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.

Nakamoto, S., et al., "A Lift-Off Method for Patterning Enzyme-Immobilized Membranes in Multi-Biosensors," Sensors and Actuators 13, 1988, pp. 165-172.

Nishida, Kenro, et al., "Clinical applications of teh wearable artifical endocrine pancreas with the newly designed needle-type glucose sensor," Elsevier Sciences B.V., 1994, pp. 353-358.

Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.

Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.

Reach, G., "A Method for Evaluating in vivo the Functional Characteristics of Glucose Sensors," Biosensors 2, 1986, pp. 211-220.

Shaw, G. W., et al., "In vitro testing of a simply constructed, highly stable glucose sensor suitable for implantation in diabetic patients," Biosensors & Bioelectronics 6, 1991, pp. 401-406.

Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, et al., "Closed-Loop Glycemic Control with a Wearable Artificial Endocrine Pancreas Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

\* cited by examiner

| $y_{t-8}$ | $y_{t-7}$ | $y_{t-6}$ | $y_{t-5}$ | $y_{t-4}$ | $y_{t-3}$ | $y_{t-2}$ | $y_{t-1}$ | $y_t$ |
|---|---|---|---|---|---|---|---|---|
| 1 | 1.5 | 2 | 2.5 | 3 | 3.5 | 4 | 4.5 | 5 |
| 1 | 1.5 | 2 | 2.5 | 3 | NULL | NULL | NULL | 3.5 |
| 1 | NULL | 1.5 | 2 | 2.5 | NULL | NULL | 4 | 5 |
| NULL | NULL | NULL | 2.5 | 3 | 3.5 | 4 | 4.5 | 5 |
| 1 | 1.5 | 2 | NULL | 3 | NULL | NULL | 4.5 | 5 |
| NULL | NULL | NULL | NULL | NULL | 3.5 | 4 | 4.5 | 5 |
| NULL | NULL | 2 | NULL | NULL | 3 | 3 | 2.75 | 2.5 |

FIG. 9

| $y_{t-8}$ | $y_{t-7}$ | $y_{t-6}$ | $y_{t-5}$ | $y_{t-4}$ | $y_{t-3}$ | $y_{t-2}$ | $y_{t-1}$ | $y_t$ | $\hat{y}$ |
|---|---|---|---|---|---|---|---|---|---|
| 1 | 1.5 | 2 | 2.5 | 3 | 3.5 | 4 | 4.5 | 5 | 7.59 |
| 1 | 1.5 | 2 | 2.5 | 3 | 3 | 3.25 | 3.38 | 3.5 | 4.67 |
| 1 | 1.25 | 1.5 | 2 | 2.5 | 3 | 3.5 | 4 | 5 | 8.12 |
| 1.38 | 1.75 | 2.13 | 2.5 | 3 | 3.5 | 4 | 4.5 | 5 | 7.48 |
| 4.5 | 4.5 | 4.5 | 4.5 | 4.5 | 4.5 | 4.5 | 4.5 | 5 | 5.66 |
| 3 | 3 | 3 | 3 | 3 | 3.5 | 4 | 4.5 | 5 | 6.89 |
| 2 | 2 | 2 | 2.33 | 2.67 | 3 | 3 | 2.75 | 2.5 | 2.41 |

FIG. 10

DATA MODIFICATION FOR PREDICTIVE OPERATIONS AND DEVICES INCORPORATING SAME

TECHNICAL FIELD

Embodiments of the subject matter described herein relate generally to medical devices, and more particularly, embodiments of the subject matter relate to modifying measurement data sequences used in controlling operations of a portable electronic device, such as a fluid infusion device.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics.

Continuous insulin infusion provides greater control of a diabetic's condition, and hence, control schemes are being developed that allow insulin infusion pumps to monitor and regulate a user's blood glucose level in a substantially continuous and autonomous manner, for example, overnight while the user is sleeping. Regulating blood glucose level is complicated by variations in the response time for the type of insulin being used along with each user's individual insulin response. Predictive algorithms may be utilized to provide estimations of the future blood glucose levels as an aid in regulating the blood glucose level. Rather than continuously sampling and monitoring a user's blood glucose level, which may compromise battery life, intermittently obtained blood glucose data samples may be utilized for determining estimations of future blood glucose levels.

Problems arise, however, when one or more blood glucose data samples intended for input to a predictive algorithm are corrupted, lost, or otherwise invalid, for example, due to noise, transmission errors, or the like. For example, in the case of recursive prediction algorithms, the prediction algorithm may be reset to eliminate the so-called "bad" data from undesirably influencing the device operation. Such an approach also incurs the lag time required for the prediction algorithm to achieve a desired level of reliability, and thus, would result in an inability to provide predictive control for periods of time.

BRIEF SUMMARY

An embodiment of a method of operating a device is provided. An exemplary method involves obtaining a sequence of measurements indicative of a condition of a user, modifying one or more unusable measurements in the sequence using one or more other measurements in the sequence to obtain a modified sequence of measurements, determining a predicted value for the condition based at least in part on the modified sequence of measurements, and operating the device in a manner that is influenced by the predicted value.

In one embodiment, a system is provided that includes a sensing arrangement and a control module coupled to the sensing arrangement. The sensing arrangement obtains a sequence of measurements of a condition. The sensing arrangement and the control module are cooperatively configured to modify a value for an unusable measurement in the sequence of measurements, resulting in a modified sequence of measurements, and determine a predicted value for the condition based at least in part on the modified sequence. The control module is configured to determine a command for operating a device in a manner that is influenced by the predicted value.

In another embodiment, an infusion system is provided. The infusion system includes a sensing arrangement and an infusion device. The sensing arrangement obtains a sequence of measurements of a condition in a body of a user, modifies a value for an unusable measurement in the sequence to obtain a modified sequence of measurements, determines a predicted value for the condition based at least in part on the modified sequence, and transmits the predicted value and a current measurement of the condition. The infusion device receives the predicted value and the current measurement. The infusion device includes a motor operable to deliver fluid to the body of the user and a control module coupled to the motor to determine a command for operating the motor based at least in part on the current measurement in a manner that is influenced by the predicted value.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

FIG. 9 depicts a table of measurement sequences suitable for use with the control process of FIG. 8;

FIG. 10 depicts a table of the measurement sequences of FIG. 9 after modifying unusable measurement samples and determining a predicted measurement value in accordance with one or more exemplary embodiments of the control process of FIG. 8.

DETAILED DESCRIPTION

Figure 1:
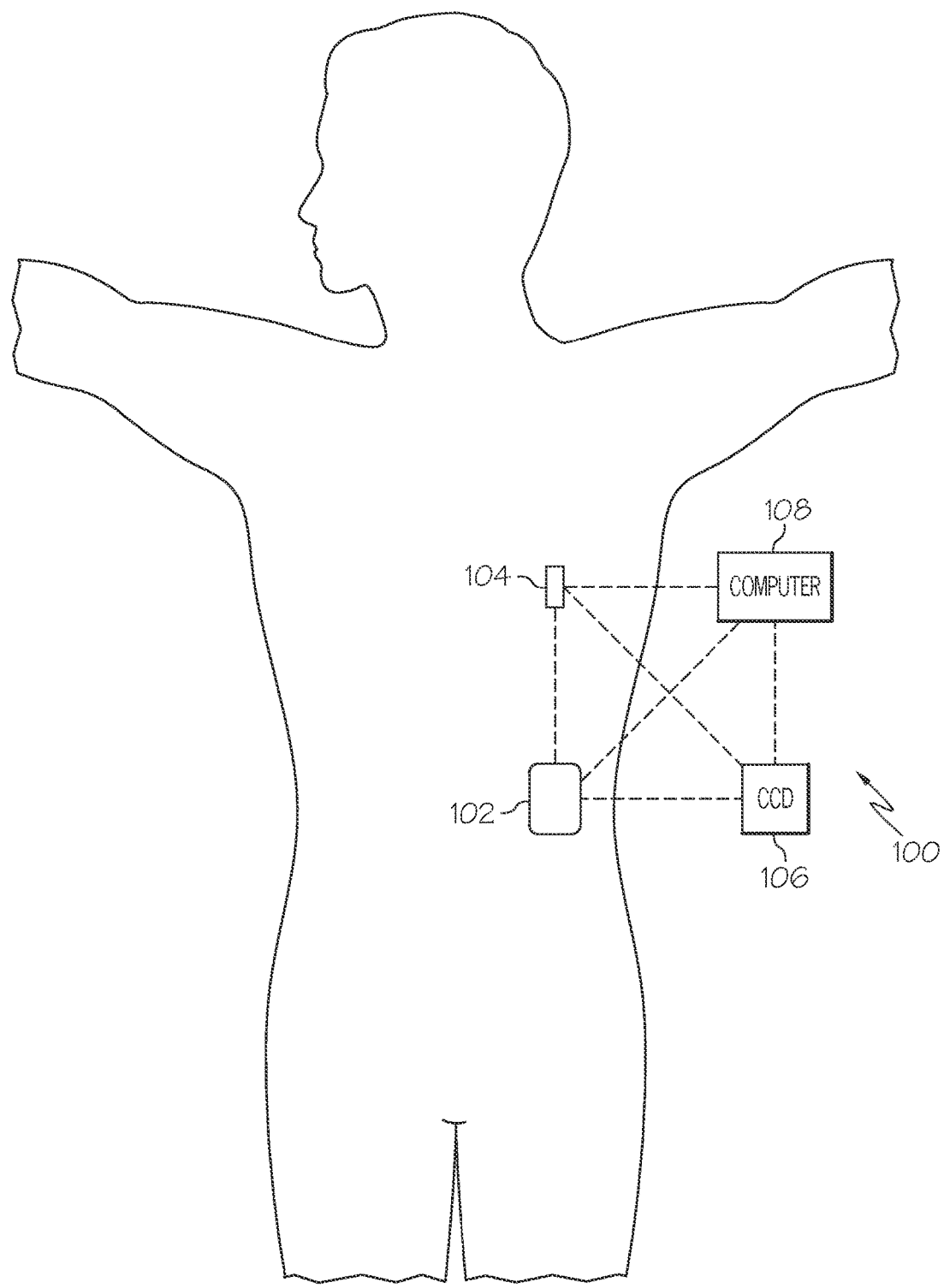
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

While the subject matter described herein can be implemented in any electronic device that includes a motor, exemplary embodiments described below are implemented in the form of medical devices, such as portable electronic medical devices. Although many different applications are possible, the following description focuses on a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Embodiments of the subject matter described herein generally relate to fluid infusion devices including a motor that is operable to linearly displace a plunger (or stopper) of a reservoir provided within the fluid infusion device to deliver a dosage of fluid, such as insulin, to the body of a user. As described in greater detail below, in exemplary embodiments, the dosage commands that govern operation of the motor are influenced by not only a current (or most recent) measurement of a condition in the body of the user, but also a predicted value (or anticipated measurement) for that condition in the body of the user at some point in the future. For example, an insulin dosage command may be determined based on a current blood glucose measurement for the user in a manner that is influenced by a predicted (or anticipated) blood glucose level in the body of the user 30 minutes into the future. In this regard, the insulin dosage command determined based on the user's current blood glucose level may be adjusted, modified, enabled and/or disabled based on the predicted blood glucose level to increase the likelihood (if not ensure) that the user's blood glucose level is maintained within an acceptable range of values going forward. While the subject matter is described herein in the context of a fluid infusion device for purposes of explanation, the subject matter is not necessarily limited to such an implementation. For example, the predicted value may be determined and/or utilized by a monitoring device to determine when and/or how the monitoring device should be operated to alert or otherwise notify a user (or one or more other individuals) of a condition in the body of the user, an operational status of an infusion device or another medical device associated with the user, and/or the like.

As described in greater detail below in the context of FIGS. 5-10, in exemplary embodiments, a predicted blood glucose level is calculated or otherwise determined as a sum of the user's current blood glucose level and a weighted estimate of the trend in the user's blood glucose level that is determined based on previously obtained blood glucose levels for the user. In exemplary embodiments, the estimate of the trend is calculated as a weighted sum of the differences between consecutive measurements that precede the current measurement. Thus, previously obtained blood glucose measurements for the user are stored or otherwise maintained for use in calculating the estimate of the trend in a deterministic manner rather than a recursive manner. In exemplary embodiments described herein, when one or more of the previously obtained blood glucose measurements are unusable for determining the predicted value, one or more other blood glucose measurements are used to obtain a modified measurement value that is substituted or otherwise used in place of the unusable blood glucose measurement. In this manner, measurements that are deemed invalid, unacceptable, or otherwise unreliable are excluded from use in determining the predicted value. Rather than disabling or otherwise resetting the prediction and/or waiting until a full sequence of consecutive usable measurements is available, the modified measurement sequence is utilized to calculate the predicted value and continue operation of the device in a manner that is influenced by the predicted value.

Turning now to FIG. 1, one exemplary embodiment of an infusion system 100 includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. patent application Ser. No. 13/049,803, the subject matter of which is hereby incorporated by reference in its entirety.

In the illustrated embodiment of FIG. 1, the infusion device 102 is designed as a portable medical device suitable for infusing a fluid, a liquid, a gel, or other agent into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

As described above, in some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

As described in greater detail below in the context of FIGS. 5-10, in exemplary embodiments, the sensing arrangement 104 and/or the infusion device 102 are cooperatively configured to determine one or more predicted values for the condition in the body of the user at one or more times in the future. Thereafter, the delivery of the fluid is influenced by the one or more predicted values indicative of the anticipated future condition of the user in addition to a recently obtained value indicative of the current condition of the user. For example, commands for operating the infusion device to deliver insulin may be determined as a function of a currently sensed blood glucose value and one or more predicted blood glucose values in a manner that accounts for the anticipated response time for the insulin and/or the user using the preceding blood glucose measurement values and/or the preceding dosage commands. To put it another way, the control of a user's blood glucose level to regulate the user's blood glucose level using the user's current blood glucose level may be influenced by one or more predicted blood glucose levels for the user in the future.

Figure 2:
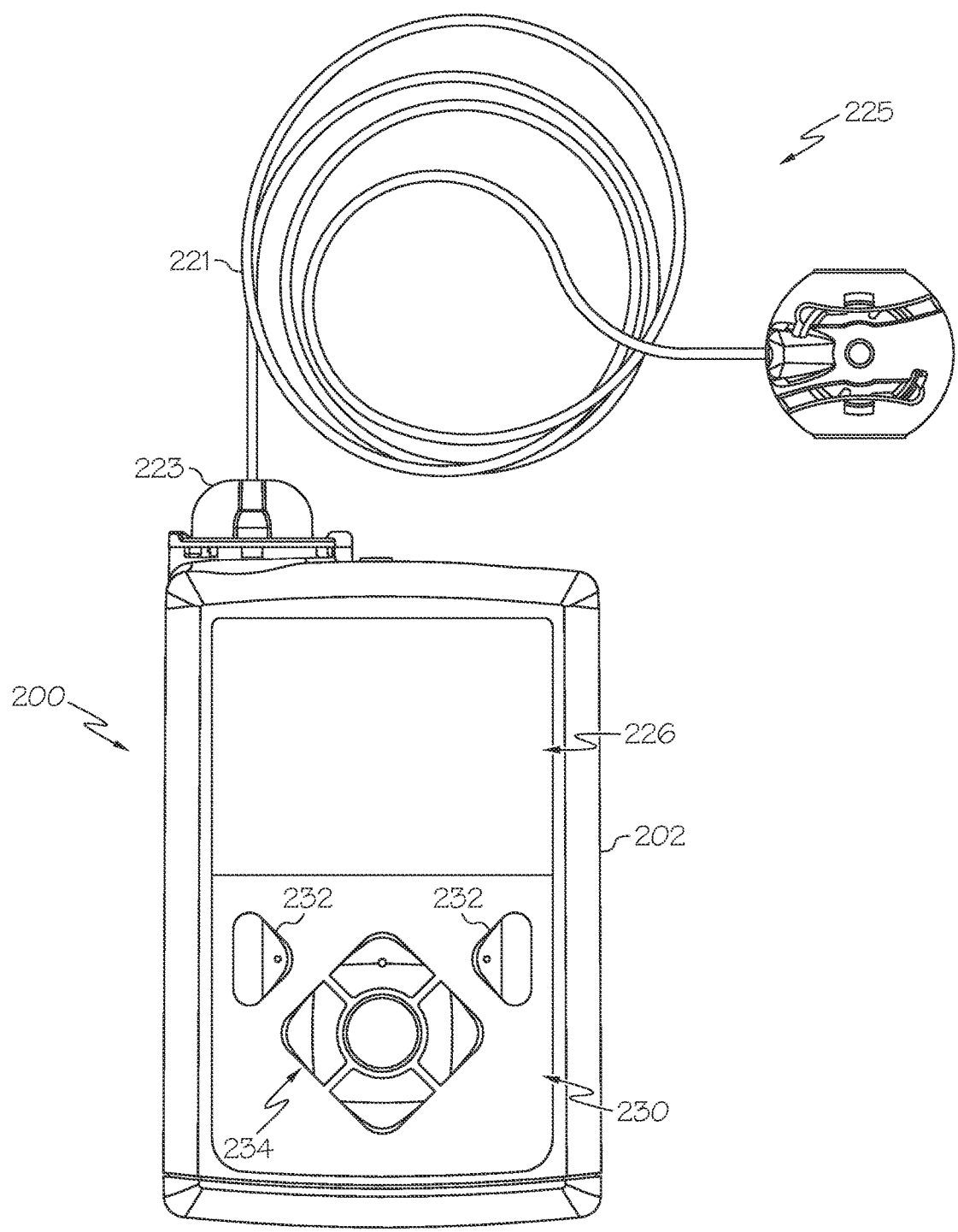
FIG. 2 depicts a plan view of an exemplary embodiment of a fluid infusion device suitable for use in the infusion system of FIG. 1.
Figure 3:
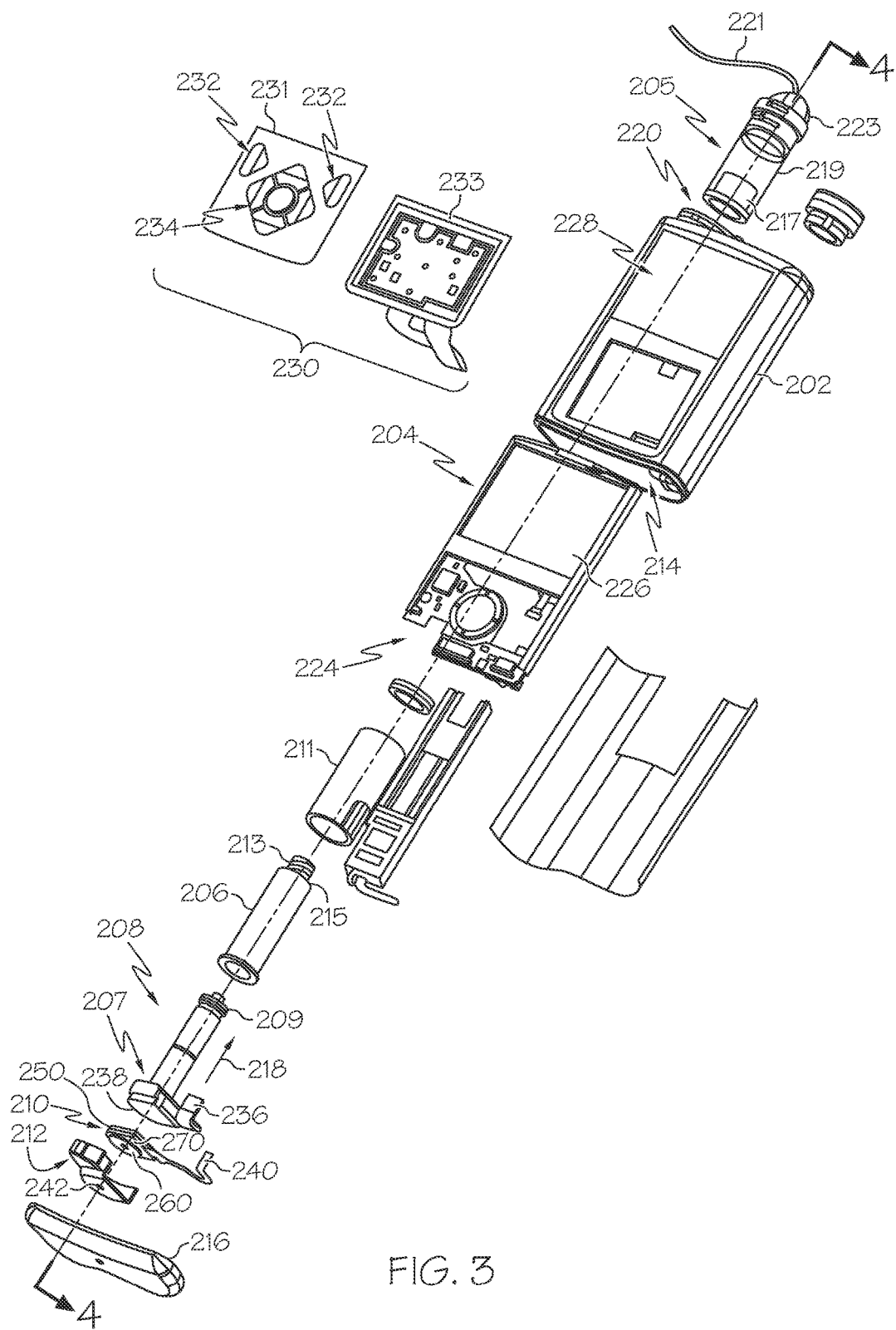
FIG. 3 is an exploded perspective view of the fluid infusion device of FIG. 2.
Figure 4:
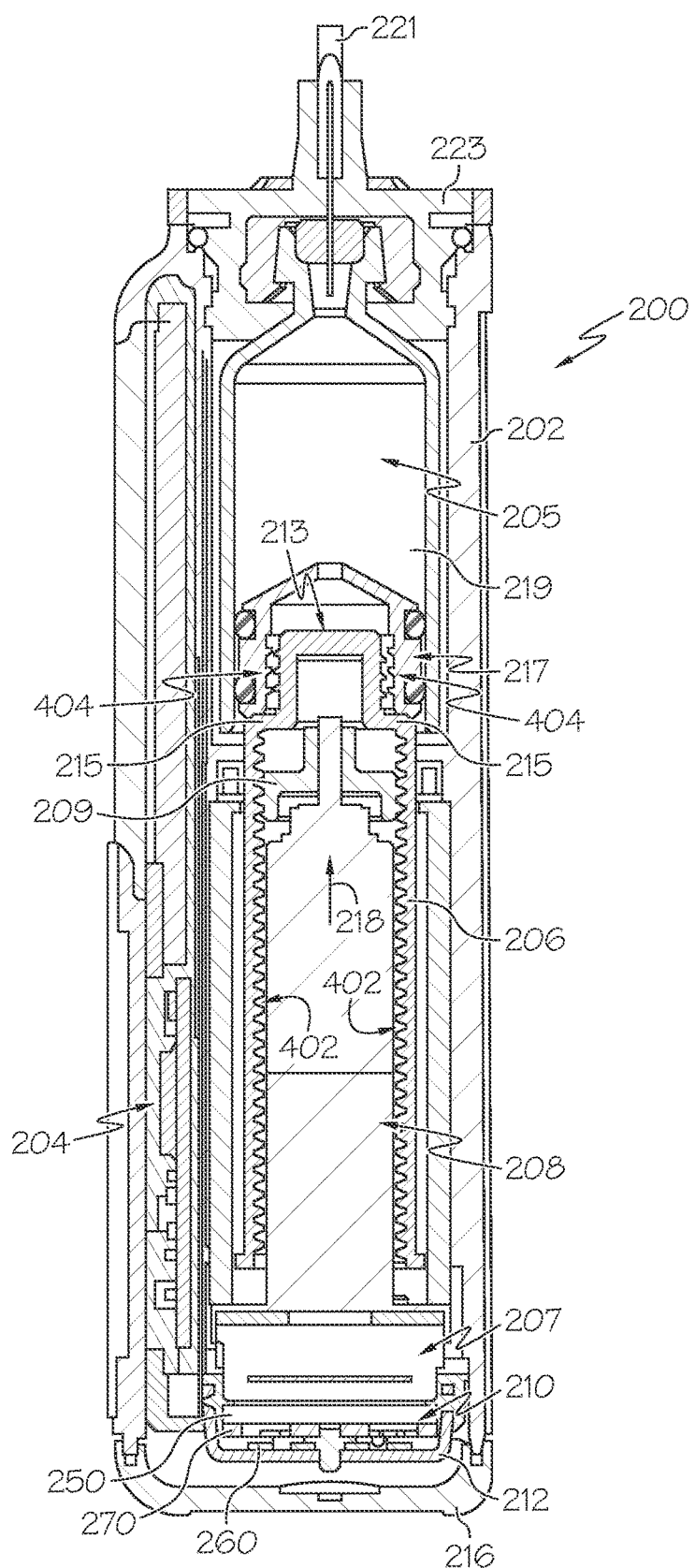
FIG. 4 is a cross-sectional view of the fluid infusion device of FIGS. 2-3 as viewed along line 4-4 in FIG. 3 when assembled with a reservoir inserted in the infusion device.

FIGS. 2-4 depict one exemplary embodiment of a fluid infusion device 200 (or alternatively, infusion pump) suitable for use in an infusion system, such as, for example, as infusion device 102 in the infusion system 100 of FIG. 1. The fluid infusion device 200 is a portable medical device designed to be carried or worn by a patient (or user), and the fluid infusion device 200 may leverage a number of conventional features, components, elements, and characteristics of existing fluid infusion devices, such as, for example, some of the features, components, elements, and/or characteristics described in U.S. Pat. Nos. 6,485,465 and 7,621,893. It should be appreciated that FIGS. 2-4 depict some aspects of the infusion device 200 in a simplified manner; in practice, the infusion device 200 could include additional elements, features, or components that are not shown or described in detail herein.

As best illustrated in FIGS. 2-3, the illustrated embodiment of the fluid infusion device 200 includes a housing 202 adapted to receive a fluid-containing reservoir 205. An opening 220 in the housing 202 accommodates a fitting 223 (or cap) for the reservoir 205, with the fitting 223 being configured to mate or otherwise interface with tubing 221 of an infusion set 225 that provides a fluid path to/from the body of the user. In this manner, fluid communication from the interior of the reservoir 205 to the user is established via the tubing 221. The illustrated fluid infusion device 200 includes a human-machine interface (HMI) 230 (or user interface) that includes elements 232, 234 that can be manipulated by the user to administer a bolus of fluid (e.g., insulin), to change therapy settings, to change user preferences, to select display features, and the like. The infusion device also includes a display element 226, such as a liquid crystal display (LCD) or another suitable display element, that can be used to present various types of information or data to the user, such as, without limitation: the current glucose level of the patient; the time; a graph or chart of the patient's glucose level versus time; device status indicators; etc.

The housing 202 is formed from a substantially rigid material having a hollow interior 214 adapted to allow an electronics assembly 204, a sliding member (or slide) 206, a drive system 208, a sensor assembly 210, and a drive system capping member 212 to be disposed therein in addition to the reservoir 205, with the contents of the housing 202 being enclosed by a housing capping member 216. The opening 220, the slide 206, and the drive system 208 are coaxially aligned in an axial direction (indicated by arrow 218), whereby the drive system 208 facilitates linear displacement of the slide 206 in the axial direction 218 to dispense fluid from the reservoir 205 (after the reservoir 205 has been inserted into opening 220), with the sensor assembly 210 being configured to measure axial forces (e.g., forces aligned with the axial direction 218) exerted on the sensor assembly 210 responsive to operating the drive system 208 to displace the slide 206. In various embodiments, the sensor assembly 210 may be utilized to detect one or more of the following: an occlusion in a fluid path that slows, prevents, or otherwise degrades fluid delivery from the reservoir 205 to a user's body; when the reservoir 205 is empty; when the slide 206 is properly seated with the reservoir 205; when a fluid dose has been delivered; when the infusion pump 200 is subjected to shock or vibration; when the infusion pump 200 requires maintenance.

Depending on the embodiment, the fluid-containing reservoir 205 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. As best illustrated in FIGS. 3-4, the reservoir 205 typically includes a reservoir barrel 219 that contains the fluid and is concentrically and/or coaxially aligned with the slide 206 (e.g., in the axial direction 218) when the reservoir 205 is inserted into the infusion pump 200. The end of the reservoir 205 proximate the opening 220 may include or otherwise mate with the fitting 223, which secures the reservoir 205 in the housing 202 and prevents displacement of the reservoir 205 in the axial direction 218 with respect to the housing 202 after the reservoir 205 is inserted into the housing 202. As described above, the fitting 223 extends from (or through) the opening 220 of the housing 202 and mates with tubing 221 to establish fluid communication from the interior of the reservoir 205 (e.g., reservoir barrel 219) to the user via the tubing 221 and infusion set 225. The opposing end of the reservoir 205 proximate the slide 206 includes a plunger 217 (or stopper) positioned to push fluid from inside the barrel 219 of the reservoir 205 along a fluid path through tubing 221 to a user.

The slide 206 is configured to mechanically couple or otherwise engage with the plunger 217, thereby becoming seated with the plunger 217 and/or reservoir 205. Fluid is forced from the reservoir 205 via tubing 221 as the drive system 208 is operated to displace the slide 206 in the axial direction 218 toward the opening 220 in the housing 202.

In the illustrated embodiment of FIGS. 3-4, the drive system 208 includes a motor assembly 207 and a drive screw 209. The motor assembly 207 includes a motor that is coupled to drive train components of the drive system 208 that are configured to convert rotational motor motion to a translational displacement of the slide 206 in the axial direction 218, and thereby engaging and displacing the plunger 217 of the reservoir 205 in the axial direction 218. In some embodiments, the motor assembly 207 may also be powered to translate the slide 206 in the opposing direction (e.g., the direction opposite direction 218) to retract and/or detach from the reservoir 205 to allow the reservoir 205 to be replaced. In exemplary embodiments, the motor assembly 207 includes a brushless DC (BLDC) motor having one or more permanent magnets mounted, affixed, or otherwise disposed on its rotor. However, the subject matter described herein is not necessarily limited to use with BLDC motors, and in alternative embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 205.

As best shown in FIG. 4, the drive screw 209 mates with threads 402 internal to the slide 206. When the motor assembly 207 is powered and operated, the drive screw 209 rotates, and the slide 206 is forced to translate in the axial direction 218. In an exemplary embodiment, the infusion pump 200 includes a sleeve 211 to prevent the slide 206 from rotating when the drive screw 209 of the drive system 208 rotates. Thus, rotation of the drive screw 209 causes the slide 206 to extend or retract relative to the drive motor assembly 207. When the fluid infusion device is assembled and operational, the slide 206 contacts the plunger 217 to engage the reservoir 205 and control delivery of fluid from the infusion pump 200. In an exemplary embodiment, the shoulder portion 215 of the slide 206 contacts or otherwise engages the plunger 217 to displace the plunger 217 in the axial direction 218. In alternative embodiments, the slide 206 may include a threaded tip 213 capable of being detachably engaged with internal threads 404 on the plunger 217 of the reservoir 205, as described in detail in U.S. Pat. Nos. 6,248,093 and 6,485,465, which are incorporated by reference herein.

As illustrated in FIG. 3, the electronics assembly 204 includes control electronics 224 coupled to the display element 226, with the housing 202 including a transparent window portion 228 that is aligned with the display element 226 to allow the display 226 to be viewed by the user when the electronics assembly 204 is disposed within the interior 214 of the housing 202. The control electronics 224 generally represent the hardware, firmware, processing logic and/or software (or combinations thereof) configured to control operation of the motor assembly 207 and/or drive system 208, as described in greater detail below in the context of FIG. 5. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 224 includes one or more programmable controllers that may be programmed to control operation of the infusion pump 200.

The motor assembly 207 includes one or more electrical leads 236 adapted to be electrically coupled to the electronics assembly 204 to establish communication between the control electronics 224 and the motor assembly 207. In response to command signals from the control electronics 224 that operate a motor driver (e.g., a power converter) to regulate the amount of power supplied to the motor from a power supply, the motor actuates the drive train components of the drive system 208 to displace the slide 206 in the axial direction 218 to force fluid from the reservoir 205 along a fluid path (including tubing 221 and an infusion set), thereby administering doses of the fluid contained in the reservoir 205 into the user's body. Preferably, the power supply is realized one or more batteries contained within the housing 202. Alternatively, the power supply may be a solar panel, capacitor, AC or DC power supplied through a power cord, or the like. In some embodiments, the control electronics 224 may operate the motor of the motor assembly 207 and/or drive system 208 in a stepwise manner, typically on an intermittent basis; to administer discrete precise doses of the fluid to the user according to programmed delivery profiles.

Referring to FIGS. 2-4, as described above, the user interface 230 includes HMI elements, such as buttons 232 and a directional pad 234, that are formed on a graphic keypad overlay 231 that overlies a keypad assembly 233, which includes features corresponding to the buttons 232, directional pad 234 or other user interface items indicated by the graphic keypad overlay 231. When assembled, the keypad assembly 233 is coupled to the control electronics 224, thereby allowing the HMI elements 232, 234 to be manipulated by the user to interact with the control electronics 224 and control operation of the infusion pump 200, for example, to administer a bolus of insulin, to change therapy settings, to change user preferences, to select display features, to set or disable alarms and reminders, and the like. In this regard, the control electronics 224 maintains and/or provides information to the display 226 regarding program parameters, delivery profiles, pump operation, alarms, warnings, statuses, or the like, which may be adjusted using the HMI elements 232, 234. In various embodiments, the HMI elements 232, 234 may be realized as physical objects (e.g., buttons, knobs, joysticks, and the like) or virtual objects (e.g., using touch-sensing and/or proximity-sensing technologies). For example, in some embodiments, the display 226 may be realized as a touch screen or touch-sensitive display, and in such embodiments, the features and/or functionality of the HMI elements 232, 234 may be integrated into the display 226 and the HMI 230 may not be present. In some embodiments, the electronics assembly 204 may also include alert generating elements coupled to the control electronics 224 and suitably configured to generate one or more types of feedback, such as, without limitation: audible feedback; visual feedback; haptic (physical) feedback; or the like.

Referring to FIGS. 3-4, in accordance with one or more embodiments, the sensor assembly 210 includes a back plate structure 250 and a loading element 260. The loading element 260 is disposed between the capping member 212 and a beam structure 270 that includes one or more beams having sensing elements disposed thereon that are influenced by compressive force applied to the sensor assembly 210 that deflects the one or more beams, as described in greater detail in U.S. patent application Ser. No. 12/908,807, which is incorporated by reference herein. In exemplary embodiments, the back plate structure 250 is affixed, adhered, mounted, or otherwise mechanically coupled to the bottom surface 238 of the drive system 208 such that the back plate structure 250 resides between the bottom surface 238 of the drive system 208 and the housing cap 216. The drive system capping member 212 is contoured to accommodate and conform to the bottom of the sensor assembly 210 and the drive system 208. The drive system capping member 212 may be affixed to the interior of the housing 202 to prevent displacement of the sensor assembly 210 in the direction opposite the direction of force provided by the drive system 208 (e.g., the direction opposite direction 218). Thus, the sensor assembly 210 is positioned between the motor assembly 207 and secured by the capping member 212, which prevents displacement of the sensor assembly 210 in a downward direction opposite the direction of arrow 218, such that the sensor assembly 210 is subjected to a reactionary compressive force when the drive system 208 and/or motor assembly 207 is operated to displace the slide 206 in the axial direction 218 in opposition to the fluid pressure in the reservoir 205. Under normal operating conditions, the compressive force applied to the sensor assembly 210 is correlated with the fluid pressure in the reservoir 205. As shown, electrical leads 240 are adapted to electrically couple the sensing elements of the sensor assembly 210 to the electronics assembly 204 to establish communication to the control electronics 224, wherein the control electronics 224 are configured to measure, receive, or otherwise obtain electrical signals from the sensing elements of the sensor assembly 210 that are indicative of the force applied by the drive system 208 in the axial direction 218.

Figure 5:
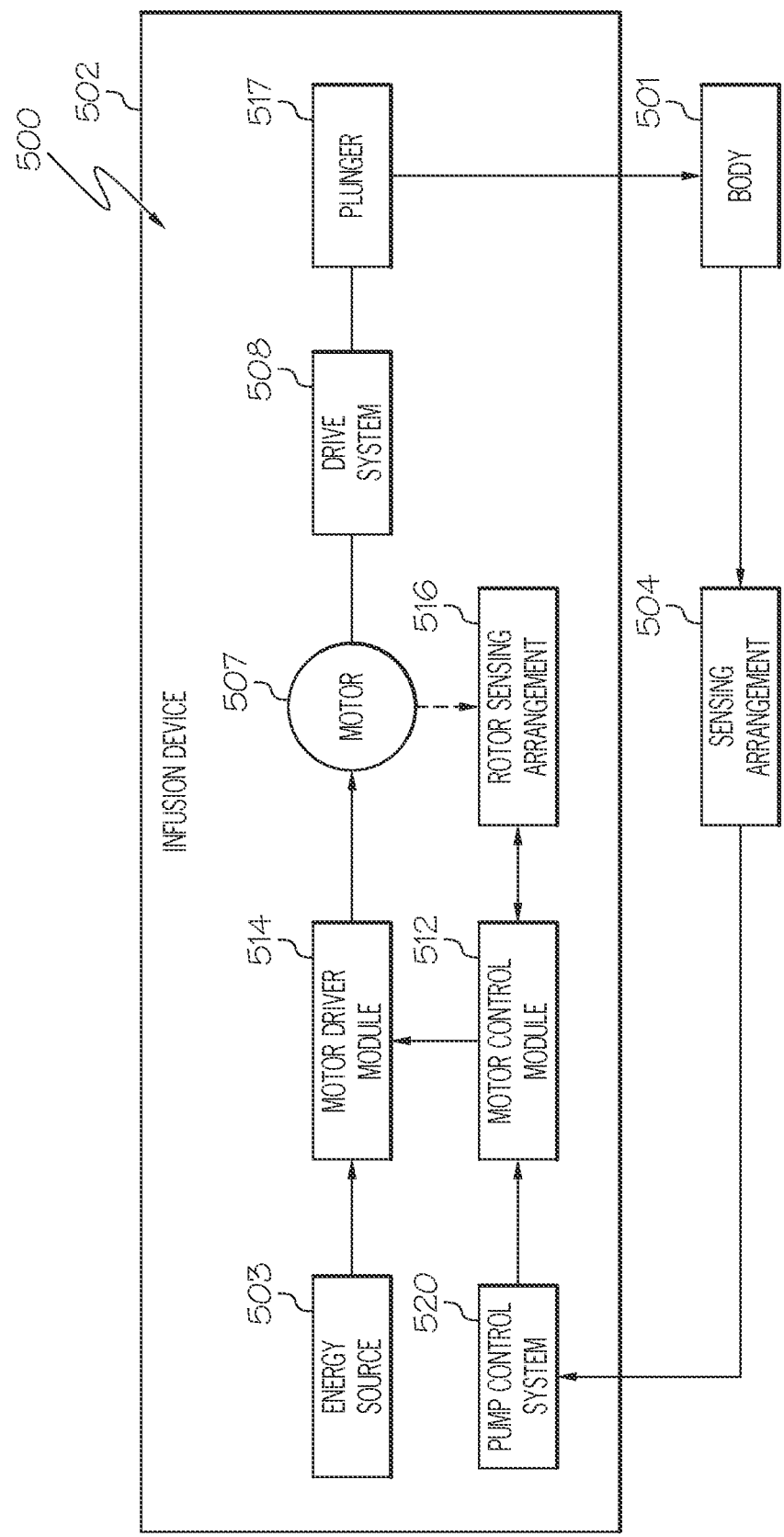
FIG. 5 is a block diagram of an exemplary control system suitable for use in a fluid infusion device, such as the fluid infusion device of FIG. 1.

FIG. 5 depicts an exemplary embodiment of a control system 500 suitable for use with an infusion device 502, such as the infusion device 102 in FIG. 1 or the infusion device 200 of FIG. 2. The control system 500 is configured to control or otherwise regulate a condition in the body 501 of a user to a desired (or target) value or otherwise maintain the condition within a range of acceptable values. In one or more exemplary embodiments, the condition being regulated is sensed, detected, measured or otherwise quantified by a sensing arrangement 504 (e.g., sensing arrangement 104) communicatively coupled to the infusion device 502. However, it should be noted that in alternative embodiments, the condition being regulated by the control system 500 may be correlative to the measured values obtained by the sensing arrangement 504. For example, the condition being regulated could be a blood glucose level or another condition that is influenced by physical activity of the user, and the sensing arrangement 504 may be realized as a heart rate monitor, a gyroscope, an accelerometer, or another suitable physiological sensor that provides measured values indicative of the level of physical activity being exhibited by the user.

It should be appreciated that FIG. 5 is a simplified representation of the infusion device 502 for purposes of explanation and is not intended to limit the subject matter described herein in any way. In this regard, more complex control schemes may be implemented by the control system 500 with multiple sensing arrangements 504 being utilized in conjunction with one another. For example, a blood glucose sensing device may be used with a heart rate monitor to implement a control scheme that regulates a user's blood glucose level based on the measured blood glucose level in a manner that accounts for the user's level of physical activity. That said, for clarity and ease of explanation, the subject matter may be described herein in the context of the control system 500 having an individual sensing arrangement 504 that senses, detects, measures or otherwise quantifies the condition being regulated.

In the illustrated embodiment, the infusion device 502 includes a motor control module 512 coupled to a motor 507 (e.g., motor assembly 207) that is operable to displace a plunger 517 (e.g., plunger 217) in a reservoir (e.g., reservoir 205) and provide a desired amount of fluid to the body 501 of a user. In this regard, displacement of the plunger 517 results in the delivery of a fluid that is capable of influencing the condition in the body 501 of the user to the body 501 of the user via a fluid delivery path (e.g., via tubing 221 of an infusion set 225). A motor driver module 514 is coupled between an energy source 503 and the motor 507. The motor control module 512 is coupled to the motor driver module 514, and the motor control module 512 generates or otherwise provides command signals that operate the motor driver module 514 to provide current (or power) from the energy source 503 to the motor 507 to displace the plunger 517 in response to receiving, from a pump control system 520, a dosage command indicative of the desired amount of fluid to be delivered. In this regard, the pump control system 520 generally represents the electronics and other components that control operation of the fluid infusion device 502 according to a desired infusion delivery program in a manner that is influenced by sensor data pertaining to a condition of a user (e.g., the user's current glucose level) received from the sensing arrangement 504 and/or in a manner that is dictated by the user. To support closed-loop control, the pump control system 520 receives or otherwise obtains a desired value (e.g., a target or command blood glucose value) for the condition in the body 501 of the user. For example, the infusion device 502 may store or otherwise maintain the target value in a data storage element accessible to the pump control system 520. Alternatively, the target value may be received from an external component (e.g., CCD 106 and/or computer 108).

In exemplary embodiments, the energy source 503 is realized as a battery housed within the infusion device 502 (e.g., within housing 202) that provides direct current (DC) power. In this regard, the motor driver module 514 generally represents the combination of circuitry, hardware and/or other electrical components configured to convert or otherwise transfer DC power provided by the energy source 503 into alternating electrical signals applied to respective phases of the stator windings of the motor 507 that result in current flowing through the stator windings that generates a stator magnetic field and causes the rotor of the motor 507 to rotate. The motor control module 512 is configured to receive or otherwise obtain a commanded dosage from the pump control system 520, convert the commanded dosage to a commanded translational displacement of the plunger 517, and command, signal, or otherwise operate the motor driver module 514 to cause the rotor of the motor 507 to rotate by an amount that produces the commanded translational displacement of the plunger 517. For example, the motor control module 512 may determine an amount of rotation of the rotor required to produce translational displacement of the plunger 517 that achieves the commanded dosage received from the pump control system 520. Based on the current rotational position (or orientation) of the rotor with respect to the stator that is indicated by the output of the rotor sensing arrangement 516, the motor control module 512 determines the appropriate sequence of alternating electrical signals to be applied to the respective phases of the stator windings that should rotate the rotor by the determined amount of rotation from its current position (or orientation). In embodiments where the motor 507 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 512 operates the motor driver module 514 to apply the determined alternating electrical signals (e.g., the command signals) to the stator windings of the motor 507 to achieve the desired delivery of fluid to the user.

When the motor control module 512 is operating the motor driver module 514, current flows from the energy source 503 through the stator windings of the motor 507 to produce a stator magnetic field that interacts with the rotor magnetic field. In some embodiments, after the motor control module 512 operates the motor driver module 514 and/or motor 507 to achieve the commanded dosage, the motor control module 512 ceases operating the motor driver module 514 and/or motor 507 until a subsequent dosage command is received. In this regard, the motor driver module 514 and the motor 507 enter an idle state during which the motor driver module 514 effectively disconnects or isolates the stator windings of the motor 507 from the energy source 503. In other words, current does not flow from the energy source 503 through the stator windings of the motor 507 when the motor 507 is idle, and thus, the motor 507 does not consume power from the energy source 503 in the idle state, thereby improving efficiency.

Depending on the embodiment, the motor control module 512 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. Furthermore, the steps of a method or algorithm described in connection with the embodiments disclosed herein may be embodied directly in hardware, in firmware, in a software module executed by the motor control module 512, or in any practical combination thereof. In exemplary embodiments, the motor control module 512 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 512. The computer-executable programming instructions, when read and executed by the motor control module 512, cause the motor control module 512 to perform the tasks, operations, functions, and processes described herein.

As described in greater detail below in the context of FIGS. 6-10, in exemplary embodiments, the pump control system 520 generates or otherwise determines the dosage commands for operating the motor 507 to displace the plunger 517 based at least in part on a measurement value indicative of the current condition in the body 501 of the user in a manner that is influenced by a predicted value for the condition. In this regard, the predicted value is calculated based at least in part on the most recent (or current) measurement value and represents an estimate of the anticipated condition in the body 501 of the user at a particular point of time in the future. In exemplary embodiments, the pump control system 520 may adjust or override the dosage command for regulating the condition of the user based on the predicted value. For example, the pump control system 520 may suspend fluid delivery (e.g., by disabling the dosage command or setting the dosage command to zero) when the predicted value falls below a suspend delivery threshold value and resume fluid delivery (e.g., by enabling the dosage command or determining a nonzero dosage command using the current measurement value) when the predicted value exceeds a resume delivery threshold value. In exemplary embodiments, the resume delivery threshold value is different from the suspend delivery threshold value. For example, the resume delivery threshold value may be equal to the suspend delivery value plus some offset value (which may be a percentage of the suspend delivery value). In other embodiments, the resume delivery threshold value may be equal to the suspend delivery threshold value.

In accordance with one or more embodiments, based on the predicted value, the pump control system 520 may adjust the dosage command for regulating the condition of the user based on the observed condition of the user and the trends in the user's condition. For example, if a predicted blood glucose level indicates that the user's blood glucose level is expected to fall below a lower threshold value, the pump control system 520 may reduce the dosage command (e.g., to zero or some other relatively smaller amount) to ensure the blood glucose level is maintained above the lower threshold value, even though the current blood glucose measurement value indicates the blood glucose level is sufficiently above the lower threshold value. Conversely, if the predicted blood glucose level indicates that the user's blood glucose level is expected to exceed an upper threshold value, the pump control system 520 may increase the dosage command to ensure the blood glucose level is maintained below the upper threshold value, even though the current blood glucose measurement value indicates the blood glucose level is sufficiently below the upper threshold value. For example, if a target blood glucose level is between a resume delivery threshold value and a suspend delivery threshold value, the pump control system 520 may decrease and/or increase the dosage command to attempt to maintain the blood glucose level between the resume delivery threshold value and the suspend delivery threshold value, and thereby improve the likelihood of the blood glucose level being maintained at or near the target value.

In some embodiments, the pump control system 520 may generate or otherwise provide an alert based on the predicted value. For example, the pump control system 520 may generate or otherwise provide an auditory and/or visual notification to the user associated with the infusion device 502 that fluid delivery can or should be suspended when the predicted value falls below a threshold value and/or that fluid delivery can or should be resumed.

In exemplary embodiments, the predicted value is calculated by adding the current measurement value to a weighted sum determined using the preceding measurement values. In this regard, a sequence of the most recently obtained measurement values for the condition in the body 501 of the user is stored or otherwise maintained. For example, in one embodiment, the predicted value is calculated using a truncated Taylor series expansion or a recursive prediction algorithm, such as a Holt-Winters exponential smoothing function. In some embodiments, the sensing arrangement 504 includes a data storage element (or memory) for storing the sensor data sequence comprised of the current measurement value and a number of preceding measurement values, as described in greater detail below in the context of FIG. 6. Additionally, in such embodiments, the sensing arrangement 504 may calculate or otherwise determine the predicted value for the condition in the body 501 of the user based on the stored sensor measurement data sequence and transmit or otherwise provide the predicted value to the pump control system 520 along with the current measurement value. Alternatively, the sensing arrangement 504 may transmit or otherwise provide the sensor measurement data sequence to the pump control system 520, which, in turn, calculates the predicted value using the sensor data sequence received from the sensing arrangement 504. In yet other embodiments, the pump control system 520 may maintain a sensor measurement data sequence comprised of the current measurement value and a number of preceding measurement values received from the sensing arrangement 504 (e.g., by queuing or buffering the most recently received current measurement values), and based on the stored sensor measurement data sequence and the current measurement value received from the sensing arrangement 504, the pump control system 520 determines the predicted value for the condition in the body 501 of the user, as described in the context of FIG. 7.

Figure 8:
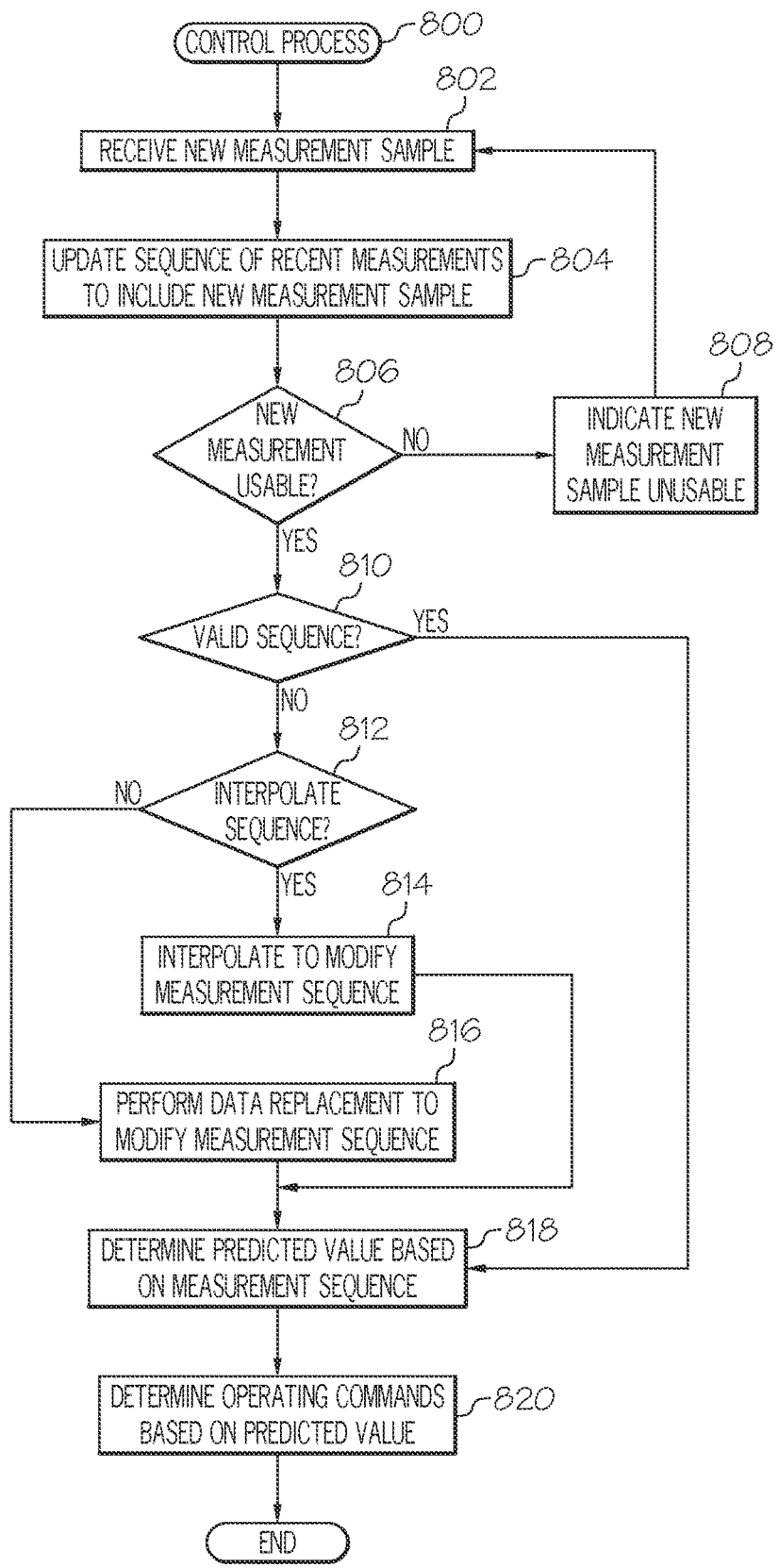
FIG. 8 is a flow diagram of an exemplary control process suitable for use with the control system of FIG. 5.

As described in the context of FIGS. 8-10, in exemplary embodiments, either the sensing arrangement 504 or the pump control system 520 analyzes or otherwise monitors the sensor measurement data sequence and/or the current measurement value to detect or otherwise identify when one or more measurement values in the sequence are invalid, unreliable, unacceptable, or otherwise unusable. In this regard, a measurement value is unusable when one or more characteristics of the measurement value is indicative of the measurement value being corrupted, unreliable, or otherwise unacceptable for purposes of determining a predicted value based thereon. In response to detecting an unusable measurement value in a sensor measurement data sequence, the sensing arrangement 504 and/or the pump control system 520 modifies the sensor measurement data sequence to ameliorate the invalid measurement value, for example, by interpolating that value in the measurement sequence using acceptable measurement values that precede and succeed the unusable measurement or replacing the unusable measurement value in the sequence with a value of a succeeding measurement value in the sequence. In this manner, by virtue of modifying the sensor measurement data sequence and calculating the predicted value in a deterministic manner, a relatively reliable predicted value may be determined and utilized without having to reset the prediction calculation (e.g., deleting or discarding the measurement sequence) and/or incur the additional lag time associated with resetting the prediction calculation and/or waiting for a complete sequence of usable values to be obtained (e.g., the time required for the data sequence to be filled with the usable measurement values).

Again, it should be understood that FIG. 5 depicts a simplified representation of the infusion device 502 for purposes of explanation and is not intended to limit the subject matter described herein in any way. In this regard, depending on the embodiment, some features and/or functionality of the sensing arrangement 504 may implemented by or otherwise integrated into the pump control system 520, or vice versa. Similarly, in practice, the features and/or functionality of the motor control module 512 may implemented by or otherwise integrated into the pump control system 520, or vice versa. Furthermore, the features and/or functionality of the pump control system 520 may be implemented by control electronics 224 located in the fluid infusion device 200, 400, while in alternative embodiments, the pump control system 520 may be implemented by a remote computing device that is physically distinct and/or separate from the infusion device 502, such as, for example, the device 106 or the device 108. Additionally, although FIG. 5 depicts the sensing arrangement 504 as being physically separate and distinct from the infusion device 502, in alternative embodiments, the sensing arrangement 504 may be integrated into or otherwise implemented by the infusion device 502 (e.g., by providing the sensing arrangement 504 within the housing 202).

Figure 6:
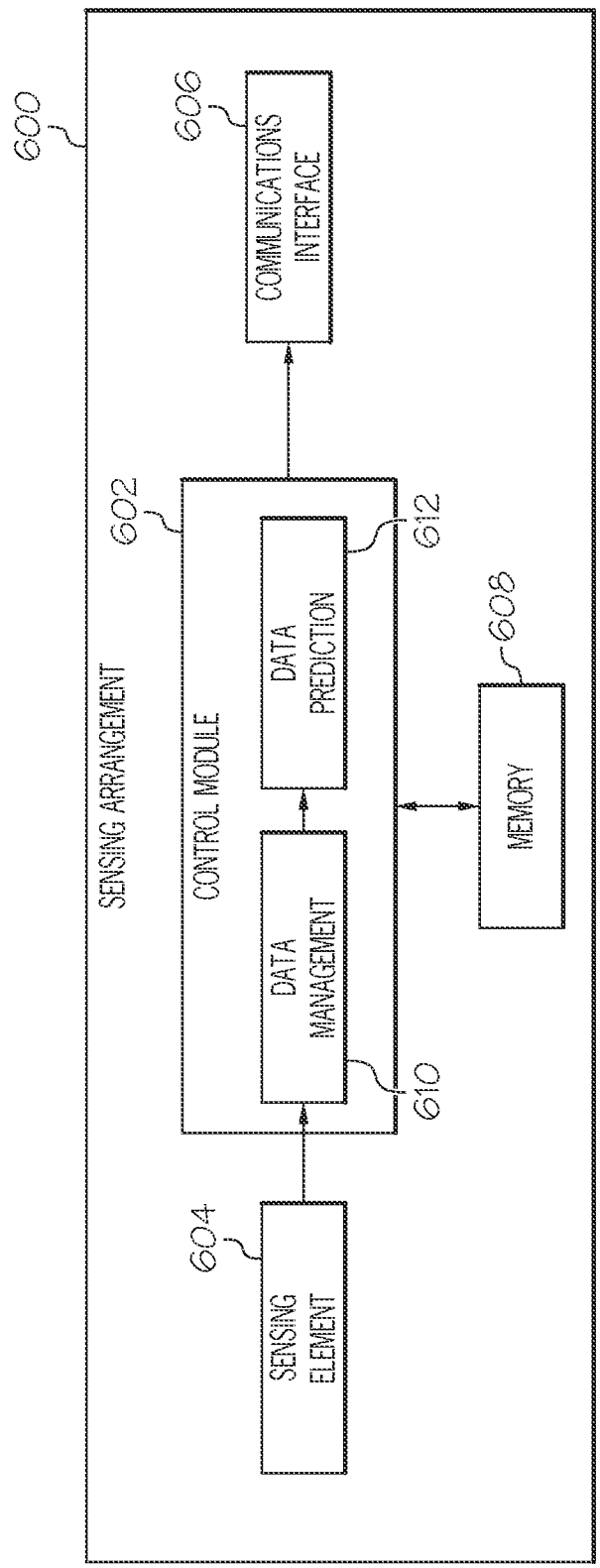
FIG. 6 is a block diagram of an exemplary sensing arrangement suitable for use in the control system of FIG. 5.

FIG. 6 depicts an exemplary embodiment of a sensing arrangement 600 suitable for use as the sensing arrangement 504 in FIG. 5 in accordance with one or more embodiments. The illustrated sensing arrangement 600 includes, without limitation, a control module 602, a sensing element 604, a communications interface 606, and a data storage element (or memory) 608. The control module 602 is coupled to the sensing element 604, the communications interface 606, and the memory 608, and the control module 602 is suitably configured to support the operations, tasks, and/or processes described herein.

The sensing element 604 generally represents the component of the sensing arrangement 600 that are configured to generate, produce, or otherwise output one or more electrical signals indicative of a characteristic that is sensed, measured, or otherwise quantified by the sensing arrangement. In this regard, a characteristic of the output electrical signal provided by the sensing element 604 corresponds or is otherwise correlative to the characteristic that the sensing element 604 senses, detects, measures, or otherwise quantifies. For example, referring to FIG. 5, the sensing element 604 may be realized as a glucose sensing element that generates an electrical signal, wherein a current (or voltage) associated with the electrical signal is correlative to the blood glucose level that is sensed or otherwise measured in the body 501 of the user.

Still referring to FIG. 6, the control module 602 generally represents the hardware, circuitry, logic, firmware and/or other component of the sensing arrangement 600 that is coupled to the sensing element 604, and the control module 602 is configured to receive the measurement data from the sensing element 604 and perform various additional tasks, operations, functions and/or operations described herein. For example, in one or more embodiments, the control module 602 implements or otherwise executes a data management application 610 that processes the measurement data received from the sensing element 604 to detect or otherwise identify whether measurement data value received from the sensing element 604 is valid or otherwise acceptable, and when a measurement data value is unacceptable, the data management application 610 substitutes a modified measurement data value for the unacceptable measurement data value in a data sequence of the most recent measurement data values. Additionally, in one or more embodiments, the control module 602 also implements or otherwise executes a data prediction application 612 that calculates or otherwise determines one or more predicted values for the characteristic sensed by the sensing element 604 based on the sequence of the most recent measurement data values received from the data management application 610. In this regard, a predicted value for the sensed characteristic at a time in the future may be influenced by or otherwise based at least in part on the modified measurement data value substituted by the data management application 610 in lieu of the unacceptable measurement data value received from the sensing element 604, as described in greater detail below.

Depending on the embodiment, the control module 602 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the control module 602, or in any practical combination thereof. In some embodiments, the control module 602 includes an analog-to-digital converter (ADC) or another similar sampling arrangement that converts the output data signal received from the sensing element 604 into corresponding digital measurement data value. For example, the control module 602 may convert an output electrical signal received from the sensing element 604 into corresponding digital measurement value (e.g., an uncalibrated glucose sensor electrical current value).

In exemplary embodiments, the control module 602 includes or otherwise accesses the data storage element or memory 608. The memory 608 may be realized using any sort of RAM, ROM, flash memory, registers, hard disks, removable disks, magnetic or optical mass storage, short or long term storage media, or any other non-transitory computer-readable medium capable of storing programming instructions for execution by the control module 602. The computer-executable programming instructions, when read and executed by the control module 602, cause the control module 602 to implement or otherwise generate the applications 610, 612 and perform the tasks, operations, functions, and processes described in greater detail below.

The communications interface 606 generally represents the hardware, circuitry, logic, firmware and/or other components of the sensing arrangement 600 that are coupled to the control module 602 and configured to support communications to/from the sensing arrangement 600. The communications interface 606 may include or otherwise be coupled to one or more transceiver modules capable of supporting wireless communications between the sensing arrangement 600 and another electronic device (e.g., an infusion device 102, 502 or another electronic device 106, 108 in an infusion system 100). Alternatively, the communications interface 606 may be realized as a port that is adapted to receive or otherwise be coupled to a wireless adapter that includes one or more transceiver modules and/or other components that support the operations of the sensing arrangement 600 described herein. In other embodiments, the communications interface 606 may be configured to support wired communications to/from the sensing arrangement 600.

It should be understood that FIG. 6 is a simplified representation of a sensing arrangement 600 for purposes of explanation and is not intended to limit the subject matter described herein in any way. In this regard, although FIG. 6 depicts the various elements residing within the sensing arrangement 600, one or more elements of the sensing arrangement 600 may be distinct or otherwise separate from the other elements of the sensing arrangement 600. For example, the sensing element 604 may be separate and/or physically distinct from the control module 602 and/or the communications interface 606. Furthermore, although FIG. 6 depicts the data management application 610 and the data prediction application 612 as being implemented by the sensing arrangement 600, in alternative embodiments, features and/or functionality of the data management application 610 and/or the data prediction application 612 may be implemented by or otherwise reside on the infusion device 102, 502 or another device 106, 108 within an infusion system 100. For example, as described in greater detail below, in some embodiments, the data management application 610 implemented by the sensing arrangement 600 may merely detect or otherwise identify unacceptable measurement data values and provide a corresponding notification of the unacceptable measurement data value to the infusion device 102, 502, which, in turn, substitutes a modified measurement data value for the unacceptable measurement data value and determines one or more predicted values for the sensed characteristic based thereon.

Figure 7:
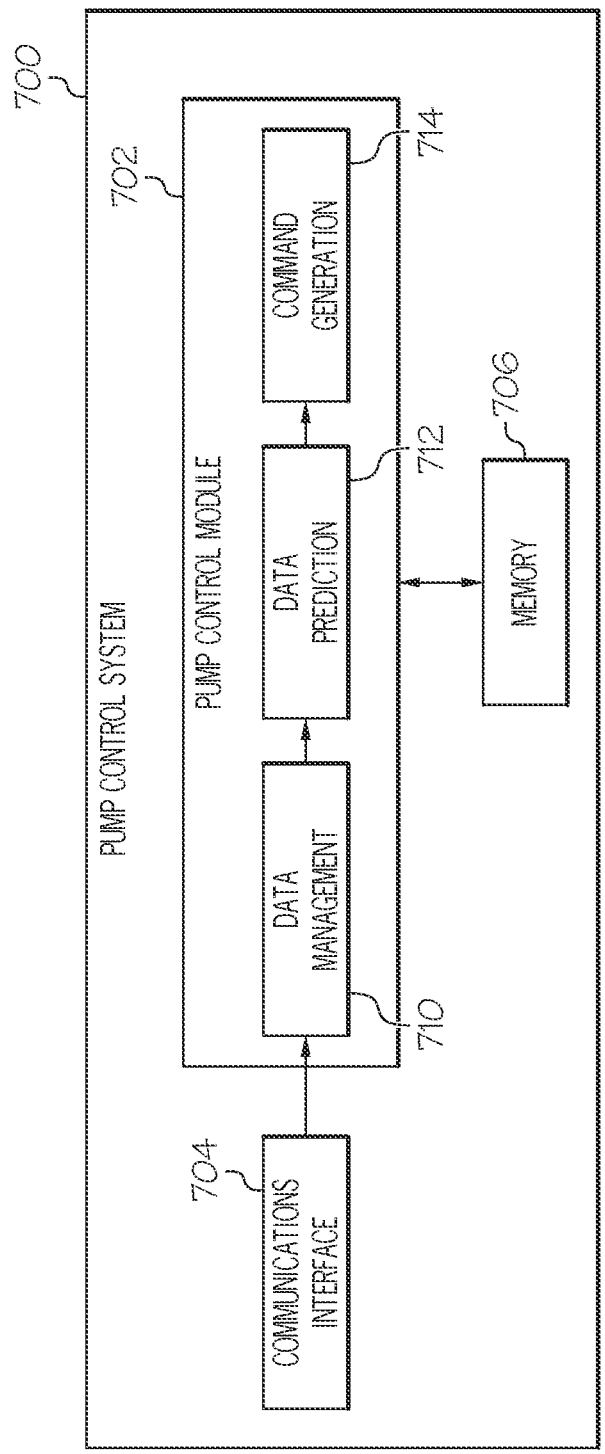
FIG. 7 is a block diagram of an exemplary pump control system suitable for use in the control system of FIG. 5.

FIG. 7 depicts an exemplary embodiment of a pump control system 700 suitable for use as the pump control system 520 in FIG. 5 in accordance with one or more embodiments. The illustrated pump control system 700 includes, without limitation, a pump control module 702, a communications interface 704, and a data storage element (or memory) 706. The pump control module 702 is coupled to the communications interface 704 and the memory 706, and the pump control module 702 is suitably configured to support the operations, tasks, and/or processes described herein.

Referring to FIG. 7 and with reference to FIG. 5, the communications interface 704 generally represents the hardware, circuitry, logic, firmware and/or other components of the pump control system 700 that are coupled to the pump control module 702 and configured to support communications between the pump control system 700 and the sensing arrangement 504. In this regard, the communications interface 704 may include or otherwise be coupled to one or more transceiver modules capable of supporting wireless communications between the pump control system 520, 700 and the sensing arrangement 504 or another electronic device 106, 108 in an infusion system 100. In other embodiments, the communications interface 704 may be configured to support wired communications to/from the sensing arrangement 504.

The pump control module 702 generally represents the hardware, circuitry, logic, firmware and/or other component of the pump control system 700 that is coupled to the communications interface 704 and configured to determine dosage commands for operating the motor 507 to deliver fluid to the body 501 based on data received from the sensing arrangement 504 and perform various additional tasks, operations, functions and/or operations described herein. For example, in exemplary embodiments, pump control module 702 implements or otherwise executes a command generation application 714 that calculates or otherwise determines a dosage command for operating the motor 507 of the infusion device 502 based at least in part on a current measurement value for a condition in the body 501 of the user, a predicted measurement value for that condition in the body 501 of the user, and one or more reference (or target) values for that condition in the body 501 of the user. For example, the command generation application 714 may determine a dosage command for operating the motor 507 to deliver insulin to the body 501 of the user based at least in part on a current blood glucose measurement value, a predicted blood glucose measurement value at a time in the future (e.g., in 30 minutes from the current time), and a reference glucose value. For example, the reference value may be equal to the threshold blood glucose value at which insulin delivery should be suspended, wherein the command generation application 714 sets the dosage command to zero to suspend operation of the motor 507 (and thereby, suspend delivery) when the current blood glucose measurement value is less than or equal to the threshold blood glucose value. Conversely, when the current blood glucose measurement value is greater than a threshold blood glucose value (e.g., the resume delivery threshold), the command generation application 714 may determine a nonzero dosage command for operating the motor 507 to deliver insulin to the body 501 of the user based at least in part on the current blood glucose measurement value. In the case of closed-loop control, the dosage command determined by the command generation application 714 may be configured to regulate the user's blood glucose level to a target blood glucose value.

Referring to FIG. 7 with reference to FIGS. 5-6, in some embodiments, the pump control module 702 may also implement or otherwise execute a data prediction application 712 and/or a data management application 710 in lieu of and/or in addition to the applications 610, 612 being implemented by the sensing arrangement 504, 600. In this regard, in some embodiments, the sensing arrangement 504, 600 may merely transmit the current measurement value and/or a sequence of recent measurement values, either with or without indications of whether those measurement values are valid and/or acceptable. In such embodiments, the data management application 710 on the pump control module 702 may process the measurement data received from the sensing arrangement 504, 600 to detect or otherwise identify whether any of the measurement data values received from the sensing arrangement 504, 600 are invalid or otherwise unacceptable. In this regard, the data management application 710 may also detect or otherwise measurement data values that were dropped, lost, or otherwise failed to be received by the communications interface 704. In a similar manner as described above, the data management application 710 substitutes a modified measurement data value for an unacceptable measurement data value to provide a modified data sequence for the most recent measurement data values. Similarly, in one or more embodiments, the pump control module 702 may also implement or otherwise execute a data prediction application 712 that calculates or otherwise determines one or more predicted values for the characteristic quantified by the sensing arrangement 504, 600 based on the sequence of the most recent measurement data values provided by the data management application 610. Thus, a predicted value for a sensed characteristic at a time in the future may be influenced by or otherwise based at least in part on the modified data sequence provided by data management application 710, as described in greater detail below.

Still referring to FIG. 7, depending on the embodiment, the control module 702 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the control module 702, or in any practical combination thereof. In exemplary embodiments, the pump control module 702 includes or otherwise accesses the data storage element or memory 708, which may be realized using any sort of non-transitory computer-readable medium capable of storing programming instructions for execution by the pump control module 702. The computer-executable programming instructions, when read and executed by the control module 702, cause the control module 702 to implement or otherwise generate one or more of the applications 710, 712, 714 and perform the tasks, operations, functions, and processes described in greater detail below.

It should be understood that FIG. 7 is a simplified representation of a pump control system 700 for purposes of explanation and is not intended to limit the subject matter described herein in any way. For example, in some embodiments where the sensing arrangement 504, 600 implements the features and/or functionality of the data management application 710 and/or the data prediction application 712, such applications 710, 712 may be absent from the pump control system 700. Furthermore, in some embodiments, the features and/or functionality of the motor control module 512 may be implemented by or otherwise integrated into the pump control system 700 and/or the pump control module 702, for example, by the command generation application 714 converting the dosage command into a corresponding motor command, in which case, the separate motor control module 512 may be absent from an embodiment of the infusion device 502.

FIG. 8 depicts an exemplary control process 800 suitable for implementation by a control system in a fluid infusion device, such as the control system 500 in the infusion device 502, to determine commands for operating a motor to deliver fluid to a user in a manner that is influenced by one or more predicted measurement values for a condition of the user at some point in the future. The various tasks performed in connection with the control process 800 may be performed by hardware, firmware, software executed by processing circuitry, or any combination thereof. For illustrative purposes, the following description refers to elements mentioned above in connection with FIGS. 1-7. In practice, portions of the control process 800 may be performed by different elements of the control system 500, such as, for example, the infusion device 502, the sensing arrangement 504, 600, the pump control system 520, 700, the motor control module 512, and/or the motor 507. It should be appreciated that the control process 800 may include any number of additional or alternative tasks, the tasks need not be performed in the illustrated order and/or the tasks may be performed concurrently, and/or the control process 800 may be incorporated into a more comprehensive procedure or process having additional functionality not described in detail herein. Moreover, one or more of the tasks shown and described in the context of FIG. 8 could be omitted from a practical embodiment of the control process 800 as long as the intended overall functionality remains intact.

In exemplary embodiments, the control process 800 initializes or otherwise begins by receiving or otherwise obtaining a new measurement data value (or sample) for a condition in the body of a user and updating a measurement data sequence of recent measurement data values for the user to include the new measurement data value (task 802, 804). In this regard, the control module 602 may sample, poll, or otherwise operate the sensing element 604 to obtain a new sample of the level of a condition in the body 501 of the user. In exemplary embodiments, the control module 602 obtains the new sample from the sensing element 604 on a regular periodic basis. For example, the control module 602 may sample the output of the sensing element 604 every five minutes to obtain a new measurement of the blood glucose level in the body 501 of the user. After obtaining a new sample, the control module 602 may obtain a stored sequence of recent measurement samples from the memory 608, add the new sample to the sequence of recent measurement samples, and shift the precedence of the previous measurement samples to follow the new measurement sample in the updated measurement sequence. For example, the sequence of recent measurement samples may be realized as a first-in first-out (FIFO) queue of measurement samples that are ordered sequentially, where the control module 602 updates the sequence of recent measurement samples by adding the measurement value for the new sample to the FIFO queue and removing the value of the oldest measurement sample from the queue. For purposes of explanation, the new or most measurement data value (or sample) may alternatively be referred to herein as the current measurement data value (or sample). In one or more embodiments, after updating the measurement data sequence, the data management application 610 stores or otherwise maintains the updated measurement sequence in memory 608, for example, by overwriting the previously stored measurement sequence. In some embodiments, the memory 608 may maintain the previously stored measurement sequence and the current (or updated) measurement sequence in memory 608 to support interpolating unusable measurement values using acceptable measurement values from the preceding stored measurement sequence, as described in greater detail below in the context of FIGS. 9-10.

Still referring to FIG. 8, the illustrated control process 800 continues by determining whether the new measurement sample is usable, and in response to determining that the new measurement sample is unusable, the control process 800 flags or otherwise indicates that the new measurement sample is unusable (tasks 806, 808). In this regard, when implemented by the sensing arrangement 504, 600, the data management application 610 applies various validation criteria and/or logic to the new measurement sample to verify that the new measurement sample is sufficiently accurate and/or reliable before the new measurement sample is capable of influencing operation of the infusion device 502. For example, the data management application 610 may ensure that the new measurement sample is greater than a minimum threshold value, less than a maximum threshold value, or otherwise within a range of acceptable valid measurement values for the condition in the body 501 of the user. Similarly, the data management application 610 may calculate or otherwise obtain one or more characteristics associated with the new measurement sample and ensure an obtained characteristic is greater than a minimum threshold value, less than a maximum threshold value, or otherwise within a range of acceptable values for that characteristic of the new measurement sample. For example, the data management application 610 may determine or obtain a signal-to-noise ratio associated with the new measurement sample and compare the signal-to-noise ratio to a minimum acceptable signal-to-noise ratio to ensure that the measurement value is not likely to have been corrupted or overly influenced by noise.

When the data management application 610 determines the new measurement sample is unusable (e.g., because its value is not within the range of acceptable valid measurement values, its signal-to-noise ratio is too low, or the like), the data management application 610 may flag or otherwise mark the new measurement sample as being invalid or otherwise unusable so that the measurement value is not utilized when determining commands for operating the motor 507 of the infusion device 502. For example, in some embodiments, the data management application 610 may replace the measurement value with an error code. In other embodiments, the sequence of recent measurement samples may maintain, in association with each respective measurement sample in the sequence, an indication of whether that respective measurement sample is acceptable or otherwise usable for subsequently determining dosage commands.

In accordance with one or more embodiments, when the current measurement sample is unusable, the sensing arrangement 504, 600 also transmits or otherwise provides the current measurement value and/or the updated measurement sample sequence to the infusion device 502 and/or the pump control system 520, 700 with a corresponding indication or notification that the current (or most recent) measurement is unacceptable. For example, the sensing arrangement 504, 600 may transmit or otherwise provide an error code for the current measurement sample or another indication that the current measurement sample is unusable or otherwise unacceptable. In some embodiments, when the infusion device 502 and/or the pump control system 520, 700 receives an error code for the current measurement sample or another an indication that the current measurement sample is unusable or otherwise unacceptable, the pump control system 520, 700 and/or the command generation application 714 may implement a modified control scheme or algorithm for determining dosage commands independent of any current and/or predicted measurement values in a manner that is likely to maintain the condition in the body 501 of the user within an acceptable range. In accordance with one embodiment, when the delivery has been suspended and more than a threshold number of unusable measurement samples have been received by the infusion device 502 while delivery is suspended, the pump control system 520, 700 and/or the command generation application 714 may automatically resume delivery.

Still referring to FIG. 8, when the new measurement sample is acceptable and usable, the control process 800 continues by determining whether the sequence of recent measurement samples is valid or otherwise acceptable for use in subsequently determining dosage commands for operating the infusion device (task 810). In this regard, the data management application 610 analyzes each measurement sample in the recent measurement sample sequence to ensure that none of the measurement samples has been flagged or otherwise identified as being unusable. When all of the measurement samples in the recent measurement sample sequence are usable, the control process 800 determines the measurement sequence is valid and acceptable and proceeds with determining a predicted measurement value for the condition in the body of the user at a time in the future and determining dosage commands for operating the infusion device in a manner that is influenced by the predicted measurement value (tasks 818, 820), in a similar manner as described below.

In exemplary embodiments, when the control process 800 determines that the sequence of recent measurement samples is invalid or otherwise unacceptable, the control process 800 continues by determining whether the recent measurement sample sequence can be interpolated to substitute modified measurement values for the measurement samples that have been flagged or otherwise identified as being unusable (task 812). In this regard, the data management application 610 determines whether the difference between two sequential usable values is less than or equal to a threshold number of measurement samples. The threshold number of measurement samples corresponds to a threshold amount of time that is short enough in duration that interpolating the recent measurement sample sequence to replace the unusable measurement samples between two sequential acceptable values allows any predicted measurement values calculated based thereon to achieve a desired level of accuracy and/or reliability. For example, if it is determined that gaps between sequential usable values that are less than or equal to 20 minutes can be interpolated and still result in predicted measurement values having a desired level of accuracy and/or reliability, then the threshold number of measurement samples may be chosen to be the number of measurement samples that would be expected to be obtained within a 20 minute timeframe. Continuing the example described above, if the new measurement samples are obtained every 5 minutes, a threshold number of measurement samples between sequential usable measurement values equal to 3 measurement samples will allow gaps of up to 20 minutes between usable measurement values to be interpolated. Thus, the data management application 610 may interpolate between any two usable measurement samples that are separated by three or fewer unusable measurement samples to obtain a modified (or adjusted) recent measurement sample sequence that does not include any invalid and/or unusable measurement values.

If the unusable measurement sample(s) in the recent measurement sample sequence can be interpolated, the control process 800 continues by performing interpolation using preceding and succeeding usable measurement samples in the measurement sequence to obtain one or more interpolated measurement values corresponding to one or more unusable measurement samples in the recent measurement sample sequence (task 814). The recent measurement sample sequence is then modified or otherwise adjusted by substituting the interpolated measurement values for the corresponding unusable measurement values, resulting in a modified (or adjusted) recent measurement sample sequence that does not include unusable measurement values for samples in the sequence that have been identified as unusable. For example, the data management application 610 may perform interpolation using any number of acceptable measurement samples that precede and/or succeed an unusable measurement sample (or consecutive unusable measurement samples) to determine interpolated measurement values for the unusable measurement sample(s). In accordance with one embodiment, the data management application 610 utilizes linear interpolation to obtain an interpolated measurement value for an unusable measurement sample(s) between two usable measurement samples. However, it should be appreciated that the subject matter described herein is not limited to any particular type of interpolation utilized to replace unusable measurement samples. In some embodiments, after modifying the measurement data sequence, the data management application 610 may store or otherwise maintain the modified measurement sequence in memory 608. In other embodiments, the data management application 610 may provide the modified measurement sequence to the data prediction application 612 while storing or otherwise maintaining the original unmodified measurement sequence in memory 608.

When the control process 800 determines recent measurement sample sequence cannot be interpolated, the control process 800 continues by replacing unusable measurement samples in the recent measurement sample sequence with the value of a more recently obtained usable measurement value (task 816). In this regard, when the number of consecutive unusable measurement samples exceeds a threshold number of measurement samples that are allowed to be interpolated (alternatively referred to herein as the interpolatable threshold), those consecutive unusable measurement samples are replaced with the more recent measurement data value that succeeds or follows those unusable measurement samples in the recent measurement sample sequence. In other words, the data management application 610 backfills consecutive unusable measurement samples that exceed the interpolatable threshold with the more recent usable measurement data value that immediately follows those consecutive unusable measurement samples. In some embodiments, any usable measurement samples that precede the consecutive unusable measurement samples in the recent measurement sample sequence are also replaced or otherwise backfilled to eliminate any potential spike, jump or other discontinuity at the transition from those prior usable measurement samples to the current measurement sample value being backfilled. For example, continuing the example described above, if the interpolatable threshold number of measurement samples is equal to 3 and the number of consecutive unusable measurement samples is greater than or equal to 4, the data management application 610 may replace the consecutive unusable measurement samples and any older measurement samples in the recent measurement sample sequence with the usable measurement value that immediately follows the consecutive unusable measurement samples in the sequence.

It should be noted that in some embodiments of the control process 800, both interpolation and replacement may be performed on a measurement data sequence to obtain a modified measurement data sequence. For example, as described in greater detail below in the context of FIGS. 9-10, in situations where there are multiple sets of consecutive unusable measurement samples in the sequence, any set of consecutive unusable measurement samples that has fewer than the interpolatable threshold number may be interpolated while any set of consecutive unusable measurement samples that has greater than the interpolatable threshold number may be replaced with the immediately following usable measurement recent value.

Additionally, it should also be noted that in some embodiments of the control process 800, when the measurement sequence is incomplete or otherwise does not contain the steady state number of measurement samples, the control process 800 may determine that the measurement sequence is not valid and acceptable (e.g., because it does not contain the desired amount of usable measurement values), in which case the control process 800 may proceed by backfilling the measurement sequence using the oldest usable measurement value in the measurement sequence. For example, the measurement sequence in memory 608 may initially be populated with an error code, a null value, or the like, thereby indicating the samples in the initial measurement sequence are not usable. If the measurement sequence contains 9 samples at steady state and the current measurement sequence contains only 2 usable samples, the control process 800 may backfill the measurement sequence with the least recent of the usable samples to obtain a complete modified measurement data sequence with the steady state number of measurement sample values. In this regard, upon initialization of the control system 500, predicted values for the condition in the body 501 of the user may still be calculated. Furthermore, in yet other embodiments, a complete modified measurement data sequence may be obtained by extrapolating the usable measurement data values backwards to fill the measurement data sequence.

Still referring to FIG. 8, after obtaining a modified recent measurement sample sequence, the control process 800 continues by determining a predicted measurement value for the condition in the body of the user at a time in the future (task 818). In exemplary embodiments, the data prediction application 612 calculates the predicted measurement value based at least in part on the current measurement data value and a weighted sum determined using the measurement data values in the recent measurement sample sequence received from the data management application 610 and/or memory 608. Thus, when one or more previously unusable measurement samples have been modified, either by interpolation or replacement with a more recent value, the predicted measurement value is calculated or otherwise determined based at least in part on those modified measurement data values in addition to the originally acceptable measurement values maintained in the modified measurement sequence.

In one or more exemplary embodiments, a predicted blood glucose level in the body 501 of the user at a time in the future is calculated using the equation $\hat{y}=y_t+hb_t$, where $\hat{y}$ is the predicted blood glucose level, $y_t$ is equal to the current (or most recent) blood glucose measurement value, h is the prediction horizon in terms of number of measurement samples in the future from the current time, and $b_t$ is the estimate of the trend in the measurements that is determined as a weighted sum of the measurement values in the recent measurement sequence. In exemplary embodiments, $b_t$ is governed by the equation $$b_t = \sum_{k=1}^{n} \beta(1-\beta)^{(k-1)} b_{t-k},$$

where $\beta$ is a tuning parameter, n is equal to the number of older blood glucose measurement values in the measurement sequence that precede the current measurement value. The $b_{t-k}$ term is calculated as the difference between the $k^{th}$ blood glucose measurement value preceding the current measurement value in the measurement sequence and the blood glucose measurement value that immediately precedes the $k^{th}$ blood glucose measurement value in the measurement sequence (e.g., $b_{t-k}=y_{t-k}-y_{t-k-1}$). In this regard, t corresponds to the current (or most recent) measurement sampling time (e.g., $y_t$ is the first or most recent measurement sample in the sequence), t–1 corresponds to the preceding (or next most recent) measurement sampling time (e.g., $y_{t-1}$ is the second most recent measurement sample in the sequence), and so on, such that $y_{t-n}$ corresponds to the oldest (or least recent) measurement sample in the sequence. It should be noted that the estimate of the trend is calculated in a deterministic manner rather than a recursive manner using a truncated Taylor series expansion of the equation $b_t=\beta(y_t-y_{t-1})+(1-\beta)b_{t-1}$, which, in turn, allows the estimate of the trend to be calculated using a modified data sequence in the event of unusable measurement samples rather than having to reinitialize the calculation. In one embodiment, the anticipated (or expected) blood glucose level in the body 501 of the user 30 minutes into the future. Thus, continuing the above example, if the measurement samples are obtained every 5 minutes, the predicted blood glucose level 30 minutes into the future (ŷ) is calculated by setting h=6, which corresponds to the number of measurement samples that would be obtained over a 30 minute duration of time.

After determining a predicted measurement value, the control process 800 continues by determining commands for operating the infusion device in a manner that is influenced by the predicted measurement value (task 820). For example, the sensing arrangement 504, 600 may transmit or otherwise provide the current blood glucose measurement value ($y_t$) and the predicted blood glucose measurement value (ŷ) in the body 501 of the user 30 minutes into the future to the pump control system 520, 700. Thereafter, the pump control system 520, 700 and/or command generation application 714 determines a dosage command based on the current blood glucose measurement value and one or more target blood glucose measurement value in a manner that is influenced by or otherwise accounts for the predicted blood glucose measurement value. For example, the pump control system 520, 700 and/or command generation application 714 may determine an initial dosage command based on a difference between the current blood glucose measurement value and a target blood glucose measurement value, and then utilize the predicted blood glucose measurement value as a modification factor that increases and/or decreases that dosage command, which is then provided to the motor control module 512 for generating appropriate motor commands. In some embodiments, the pump control system 520, 700 and/or command generation application 714 may set the dosage command to zero when the predicted blood glucose value is less than a lower threshold blood glucose level. As described above in the context of FIG. 5, in response to receiving a dosage command, the motor control module 512 may convert the dosage command to a corresponding motor command (e.g., a number of steps of rotor rotation) that will displace the plunger 517 by an amount corresponding to the desired dosage and then operate the motor 507 to achieve the desired displacement of the plunger 517. In this manner, delivery of the desired amount of fluid from the infusion device 502 to the body 501 of the user is achieved.

Still referring to FIG. 8, while the foregoing discussion of the control process 800 was described in the context of the sensing arrangement 504, 600 detecting or otherwise identifying acceptable and/or unusable measurement samples and/or measurement sequences, modifying measurement sequences, and determining predicted measurement values, in alternative embodiments, one or more of those aspects may be performed by the infusion device 502 and/or the pump control system 520, 700. For example, in one alternative embodiment, the sensing arrangement 504, 600 may merely obtain a new measurement value and transmit the new measurement value to the pump control system 520, 700, whereby the data management application 710 on the pump control module 702 manages or otherwise maintains the sequence of recent measurement values and determines whether the new measurement value is acceptable. In such embodiments, the pump control system 520, 700 may also account for measurement values that may have been dropped or otherwise lost in transmission from the sensing arrangement 504, 600 that were not received by the communications interface 704. For example, if the sensing arrangement 504, 600 obtains and transmits a new measurement value every 5 minutes, the data management application 710 may automatically identify an absent measurement sample and update the measurement sequence to reflect a new unusable measurement sample in response to a failure to receive a new measurement value 5 minutes (plus or minus a particular time window or margin for error) after the most recently obtained measurement sample. In a similar manner as described above, the data management application 710 on the pump control module 702 may also detect or otherwise identify an unacceptable and/or invalid data sequence and modify the measurement sequence using one or more acceptable measurement values within the measurement sequence (e.g., tasks 810, 812, 814, 816). Thereafter, the data prediction application 712 on the pump control module 702 determines a predicted measurement value that is provided to the command generation application 714 for generating operating commands for the infusion device 502 (e.g., tasks 818, 820), as described above.

In one or more embodiments, the sensing arrangement 504, 600 obtains new measurement values, updates the measurement sequences, and transmits the measurement sequences with a corresponding indication of any unusable measurement values in a measurement sequence (e.g., tasks 802, 804, 806, 808). In such embodiments, the data management application 710 on the pump control module 702 receives a measurement sequence from the sensing arrangement 504, 600 and determines whether the measurement sequence needs to be modified for subsequent usage (e.g., task 810). In this regard, the data management application 710 may modify unusable measurement values indicated by the sensing arrangement 504, 600 while also accounting for any measurement samples that may have been dropped or otherwise lost in transmission from the sensing arrangement 504, 600. For example, the data management application 710 may also identify absent or missing measurement samples within a measurement sequence received from the sensing arrangement 504, 600 that were likely dropped, lost, or otherwise corrupted during transmission.

FIG. 9 is depicts a table 900 including exemplary measurement sequences, and FIG. 10 depicts a table 1000 corresponding to the measurement sequences in the table 900 of FIG. 9 after invalid and/or unacceptable measurement sequences have been modified and a corresponding predicted value based thereon has been calculated using a in conjunction with the control process 800 described above. In FIG. 9, unusable measurement samples are identified by setting the corresponding measurement value to a null value. As described above, the unusable measurement samples could be measurement samples that did not result in a valid measurement value (e.g., an original measurement value outside the range of valid values for the sensing element 604), measurement samples having a low signal-to-noise ratio that are susceptible to being corrupted by noise, absent measurement samples that were lost or otherwise failed to be received by the infusion device 502, or the like. The first row of the tables 900, 1000 depicts a valid measurement sequence where all of the individual measurement samples are originally valid and acceptable. In the illustrated embodiment, the predicted values depicted in the table 1000 are calculated for the time 6 measurement samples into the future (e.g., h=6) with a tuning parameter of 0.3 (e.g., β=0.3).

The second row in the table 900 depicts a measurement sequence where a difference between two sequential usable measurement samples (e.g., $y_t$ and $y_{t-4}$) is equal to interpolatable number of measurement samples (e.g., 3 measurement samples corresponding to an allowable gap of 20 minutes between $y_t$ and $y_{t-4}$). The second row in table 1000 depicts the modified measurement sequence obtained by performing linear interpolation between the usable measurement values for $y_t$ and $y_{t-4}$ to replace the measurement samples between $y_t$ and $y_{t-4}$ with interpolated measurement values and the corresponding predicted measurement value calculated using those interpolated measurement values.

The third row in the table 900 depicts a measurement sequence where the difference between usable measurement samples $y_{t-8}$ and $y_{t-6}$ and the difference between usable measurement samples $y_{t-4}$ and $y_{t-1}$ are both less than or equal to the interpolatable number of measurement samples. The third row in table 1000 depicts the modified measurement sequence obtained by performing linear interpolation between the usable measurement values for $y_{t-8}$ and $y_{t-6}$ to obtain an interpolated value for $y_{t-7}$ and performing linear interpolation between the usable measurement values for $y_{t-4}$ and $y_{t-1}$ to obtain interpolated values for $y_{t-3}$ and $y_{t-2}$.

The fourth row in the tables 900, 1000 depicts a modified measurement sequence where a usable measurement sample (e.g., $y_{t-9}$) from a previously stored measurement sequence in memory 608, 706 is used to interpolate and replace the oldest measurement sample(s) in a current measurement sequence when the next preceding measurement value was an acceptable measurement value (e.g., $y_{t-9}=1$).

The fifth row in the table 900 depicts a measurement sequence where the difference between two sequential usable measurement samples $y_{t-1}$ and $y_{t-6}$ is greater than the interpolatable number of measurement samples. The fifth row in table 1000 depicts the modified measurement sequence obtained by backfilling or otherwise replacing measurement samples older than $y_{t-1}$ with the measurement value for $y_{t-1}$. In this regard, originally acceptable measurement values for $y_{t-6}$, $y_{t-7}$, and $y_{t-8}$ may be overwritten with the value of $y_{t-1}$. In this manner, backfilling for $y_{t-6}$, $y_{t-7}$ and $y_{t-8}$ eliminates the spike or jump that could otherwise occur when transitioning from the original value of $y_{t-6}$ (e.g., 2) to the backfilled value for $y_{t-5}$ (e.g., 4.5) and effectively resets the prediction algorithm with the value of $y_{t-1}$.

The sixth row in the tables 900, 1000 depicts a modified measurement sequence where the oldest measurement samples are unusable and replaced with the value of the usable measurement sample that succeeds the unusable measurement samples in the sequence.

The seventh row in the table 900 depicts a measurement sequence where the oldest two measurement samples in the sequence are unusable and cannot be interpolated because the preceding measurement sample (e.g., $y_{t-9}$) is unavailable or unusable. At the same time, the difference between usable samples $y_{t-3}$ and $y_{t-6}$ is less than the interpolatable number of measurement samples. In this regard, the seventh row in table 1000 depicts the modified measurement sequence obtained by backfilling or otherwise replacing measurement samples $y_{t-7}$ and $y_{t-8}$ with the usable measurement value for $y_{t-6}$, while also performing linear interpolation between the usable measurement values for $y_{t-3}$ and $y_{t-6}$ to obtain interpolated values for $y_{t-4}$ and $y_{t-5}$.

As described above, by virtue of calculating the predicted measurement value in a deterministic manner rather than a recursive manner, any measurement values that are invalid, unacceptable, or otherwise missing from a measurement sequence may be interpolated or replaced using acceptable measurement value(s) to obtain a modified measurement sequence, which may then be utilized to calculate a predicted measurement value without compromising the accuracy and/or reliability of the prediction. In this regard, a predicted measurement value remains available to the pump control system 520, 700 for influencing operation of the infusion device 502, rather than having to disable the predictive control and wait until a complete and valid measurement sequence is available before resuming the predictive control.

For the sake of brevity, conventional techniques related to glucose sensing and/or monitoring, sensor calibration and/or compensation, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A system comprising:
   a sensing arrangement to obtain a sequence of measurements of a condition in a body of a user, the sensing arrangement including a sensing element providing a signal indicative of the condition; and
   a control module coupled to the sensing arrangement, the sensing arrangement and the control module being cooperatively configured to identify one or more unusable measurements in the sequence of measurements, modify a value for the one or more unusable measurements in the sequence of measurements, resulting in a modified sequence of measurements, determine an estimate of a trend in the sequence of measurements based at least in part on differences between consecutive measurements of the modified sequence of measurements, and determine a predicted value for the condition in the body of the user at a time in the future based at least in part on a current value for the condition and the estimate of the trend, wherein:
   the one or more unusable measurements are replaced in the modified sequence with an interpolated value based on a preceding usable measurement in the sequence and a succeeding usable measurement in the sequence when a number of measurement samples corresponding to a gap between the preceding usable measurement and the succeeding usable measurement is less than an interpolation threshold;
   the one or more unusable measurements are backfilled with the succeeding usable measurement when the number of measurement samples corresponding to the gap is greater than the interpolation threshold; and the control module is configured to operate a medical device in a manner that is influenced by the predicted value.

2. The system of claim 1, wherein the sensing arrangement identifies the one or more unusable measurements in the sequence, modifies the value using one or more acceptable measurements in the sequence to obtain the modified sequence, determines the predicted value based at least in part on the modified sequence, and provides the predicted value to the control module.

3. The system of claim 1, wherein:
the sensing arrangement identifies the one or more unusable measurements in the sequence, modifies the value using one or more acceptable measurements in the sequence to obtain the modified sequence, and provides the modified sequence to the control module; and
the control module determines the predicted value based at least in part on the modified sequence received from the sensing arrangement.

4. The system of claim 1, the sensing arrangement transmitting the sequence of measurements to the medical device including the control module, wherein the control module identifies the one or more unusable measurements in the sequence, modifies the value using one or more acceptable measurements in the sequence to obtain the modified sequence, and determines the predicted value based at least in part on the modified sequence.

5. The system of claim 1, the medical device comprising an insulin infusion device including the control module, wherein:
the sensing arrangement obtains a sequence of blood glucose measurements; and
the sensing arrangement and the control module are cooperatively configured to determine a predicted blood glucose measurement value based at least in part on the modified sequence of blood glucose measurements; and
the control module determines a dosage command for operating the insulin infusion device to deliver insulin in a manner that is influenced by the predicted blood glucose measurement value.

6. The system of claim 5, wherein:
the insulin infusion device includes a motor operable to displace a plunger to deliver the insulin to the body of the user; and
the motor is operated in a manner that is influenced by the dosage command.

7. An infusion system comprising:
a sensing arrangement to obtain a sequence of measurements of a condition in a body of a user, identify one or more unusable measurements in the sequence of measurements, modify a value for the one or more unusable measurements in the sequence to obtain a modified sequence of measurements, determine an estimate of a trend in the sequence of measurements based at least in part on differences between consecutive measurements of the modified sequence of measurements, determine a predicted value for the condition in the body of the user at a time in the future based at least in part on the estimate of the trend and a current measurement of the condition, and transmit the predicted value and the current measurement of the condition, wherein:

the sensing arrangement includes a sensing element providing a signal indicative of the condition;
the one or more unusable measurements are replaced in the modified sequence with an interpolated value based on a preceding usable measurement in the sequence and a succeeding usable measurement in the sequence when a number of measurement samples corresponding to a gap between the preceding usable measurement and the succeeding usable measurement is less than an interpolation threshold; and
the one or more unusable measurements are backfilled with the succeeding usable measurement when the number of measurement samples corresponding to the gap is greater than the interpolation threshold; and
an infusion device to receive the predicted value and the current measurement, the infusion device including:
a motor operable to deliver fluid to the body of the user; and
a control module coupled to the motor to operate the motor based at least in part on the current measurement in a manner that is influenced by the predicted value.

8. The system of claim 1, wherein the control module modifies the value for the one or more unusable measurements by replacing one or more unusable measurements with a modified measurement value.

9. The system of claim 8, wherein the modified measurement value comprises a value of a succeeding usable measurement in the sequence.

10. The system of claim 8, wherein the modified measurement value comprises an interpolated value based on a preceding usable measurement and a succeeding usable measurement in the sequence.

11. The system of claim 8, wherein the modified measurement value comprises a value of a succeeding usable measurement in the sequence.

12. The system of claim 8, wherein the modified measurement value comprises an interpolated value based on a preceding usable measurement and a succeeding usable measurement in the sequence.

13. The system of claim 1, wherein:
the medical device comprises an infusion device capable of delivering fluid to the user;
the fluid influences the condition of the user; and
the command operates a motor of the infusion device to deliver the fluid to the user.

14. The system of claim 13, wherein:
the fluid comprises insulin;
the sequence of measurements comprises a sequence of blood glucose measurements; and
the predicted value comprises a predicted blood glucose for the user at a time in the future based at least in part on the modified sequence.

15. The system of claim 1, the modified sequence including a current measurement for the condition, wherein:
the estimate of the trend comprises a first weighted sum of the differences between consecutive measurements in the modified sequence that precede the current measurement; and
the predicted value comprises a second weighted sum of the current measurement and the estimate of the trend.

16. The system of claim 15, wherein the estimate of the trend comprises a Taylor series expansion using the differences between consecutive measurements.

17. The system of claim 1, wherein the predicted value is calculated using a recursive prediction algorithm.

18. The system of claim 17, wherein the recursive prediction algorithm comprises a Holt-Winters exponential smoothing function.

19. The system of claim 1, wherein:
the estimate of the trend is calculated using a truncated Taylor series expansion of the equation $b_t = \beta(y_t - y_{t-1}) + (1-\beta)b_{t-1}$; and
the predicted value is governed by the equation $\hat{y} = y_t + hb_t$, wherein:
$\hat{y}$ is the predicted value;
$y_t$ is equal to a most recent measurement in the sequence of measurements;
h is a prediction horizon number of measurement samples in the future;
$b_t$ is the estimate of the trend; and
$\beta$ is a tuning parameter.

20. The infusion system of claim 7, wherein the estimate of the trend is calculated in a deterministic manner using a truncated Taylor series expansion.

* * * * *